United States Patent
Sughrue et al.

(10) Patent No.: US 11,515,041 B1
(45) Date of Patent: Nov. 29, 2022

(54) DISPLAY OF SUBSET BRAIN GRAPH BY SHADING NODES

(71) Applicant: Omniscient Neurotechnology Pty Limited, Sydney (AU)

(72) Inventors: Michael Edward Sughrue, Sydney (AU); Stephane Philippe Doyen, Glebe (AU); Kieran Mann, San Diego, CA (US); Xinling Jiang, Willoughby (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 17/465,811

(22) Filed: Sep. 2, 2021

(51) Int. Cl.
| | | |
|---|---|---|
| *G06F 17/00* | (2019.01) | |
| *G16H 50/20* | (2018.01) | |
| *G16H 50/50* | (2018.01) | |
| *G06F 3/04847* | (2022.01) | |
| *G06T 11/60* | (2006.01) | |
| *A61B 8/08* | (2006.01) | |
| *A61B 6/00* | (2006.01) | |

(52) U.S. Cl.
CPC ......... *G16H 50/20* (2018.01); *G06F 3/04847* (2013.01); *G06T 11/60* (2013.01); *G16H 50/50* (2018.01); *A61B 6/501* (2013.01); *A61B 8/0808* (2013.01); *G06T 2200/24* (2013.01); *G06T 2210/41* (2013.01)

(58) Field of Classification Search
CPC .... G16H 50/20; G16H 50/50; G06F 3/04847; G06F 3/04842; G06F 16/444; G06F 16/48; G06F 3/04815; G06T 11/60; G06T 2200/24; G06T 2210/41; A61B 6/501; A61B 8/0808

USPC ......................................................... 715/771
See application file for complete search history.

(56) References Cited

U.S. PATENT DOCUMENTS

| | | | | |
|---|---|---|---|---|
| 6,240,308 B1* | 5/2001 | Hardy | .................... | A61B 90/10 |
| | | | | 600/424 |
| 2007/0167788 A1* | 7/2007 | Hartlep | ..................... | G06T 7/12 |
| | | | | 600/447 |
| 2007/0203546 A1* | 8/2007 | Stone | ................. | A61N 1/36082 |
| | | | | 607/59 |
| 2008/0103385 A1* | 5/2008 | Ma | .......................... | G06T 19/20 |
| | | | | 600/416 |
| 2009/0220136 A1* | 9/2009 | Bova | ...................... | A61B 90/36 |
| | | | | 382/285 |

(Continued)

*Primary Examiner* — Jason T Edwards
(74) *Attorney, Agent, or Firm* — Fish & Richardson P.C.

(57) ABSTRACT

Disclosed herein are systems and methods for interactive graphical user interfaces (GUIs) that users (e.g., medical professionals) can use to interact with modelled versions of brains and easily and intuitively analyze deep and/or lateral structures in the brain. A user can, for example, selectively view structures and their connectivity data (e.g., nodes and edges) relative to other structures and connectivity data over a representation of a particular patient's brain. Emphasis can be minimized for certain foreground nodes and edges (e.g., lateral structures) to make it easier for the user to focus on and analyze deeper structures that otherwise can be challenging to visualize and understand. A method can include overlaying deep and non-deep nodes on a representation of a brain, displaying the representation of the brain in a GUI, receiving user input indicating interest in focusing on one or more deep nodes, and taking an action based on the input.

20 Claims, 9 Drawing Sheets

(56) References Cited

U.S. PATENT DOCUMENTS

| | | | |
|---|---|---|---|
| 2010/0312096 A1* | 12/2010 | Guttman | A61B 34/25 600/411 |
| 2011/0028825 A1* | 2/2011 | Douglas | G06T 19/00 600/407 |
| 2012/0015316 A1* | 1/2012 | Sachdeva | G06T 19/20 382/128 |
| 2012/0080616 A1* | 4/2012 | Schoenborn | A61B 5/0071 250/459.1 |
| 2012/0172700 A1* | 7/2012 | Krishnan | A61B 6/505 600/407 |
| 2014/0081659 A1* | 3/2014 | Nawana | A61B 5/4833 705/3 |
| 2014/0181754 A1* | 6/2014 | Mori | G06T 19/00 715/847 |
| 2014/0379356 A1* | 12/2014 | Sachdeva | A61C 7/002 705/2 |
| 2016/0110904 A1* | 4/2016 | Jeon | A61B 5/4076 382/131 |
| 2016/0283676 A1* | 9/2016 | Lyon | G06Q 40/08 |
| 2018/0137689 A1* | 5/2018 | Eastwood | G06T 7/11 |
| 2019/0350659 A1* | 11/2019 | Wang | A61B 90/00 |
| 2020/0054398 A1* | 2/2020 | Kovtun | G16H 40/63 |
| 2020/0098125 A1* | 3/2020 | Langeland | G06T 7/70 |
| 2020/0167912 A1* | 5/2020 | Xu | G06T 7/11 |
| 2021/0209406 A1* | 7/2021 | Yuzawa | A61B 5/7264 |
| 2022/0067925 A1* | 3/2022 | Massarwa | G06T 7/11 |

* cited by examiner

DISPLAY OF SUBSET BRAIN GRAPH BY SHADING NODES

TECHNICAL FIELD

The subject matter described herein generally relates to processing images of brains and displaying information about the brains using an interactive brain navigation system and interface.

BACKGROUND

Medical imaging includes techniques and processes for creating visual representations of an interior of a body for clinical analysis and medical intervention, as well as visual representation of physiology of some organs or tissues. Medical imaging can reveal internal structures hidden by skin and bones, and can be used to diagnose and treat various diseases. Medical imaging also can establish a database of normal anatomy and physiology to make it possible to identify abnormalities amongst cohorts. Some medical imaging can also provide insights into functional activity and structural connections of a brain.

SUMMARY

This document generally describes technologies for processing medical images of brains and/or displaying the processed images in a user-interactive brain navigation system (e.g., interface). The disclosed technology can be used by clinicians and other medical professionals to glean insight about structures and connections in a subject's brain (e.g., patient, human, animal, or other specimen). Based on such insights, the clinicians and other medical professionals can perform improved and more informed diagnoses, treatments, operations, and/or research than with existing systems.

For example, brain surgery can involve making cuts into the brain. In order to perform brain surgery, one can use a standard brain atlas containing a standard parcellation scheme, regardless of the specifics of the particular brain being considered. The term "parcellation" refers to the process of delineating regions of the brain that have similar properties between individuals, such as functional activity, cytoarchitecture, and structural connectivity. In this nomenclature, a "parcellation" is a region of the brain (e.g., cortex) that can be shown to have similar properties across individuals, even if the exact boundaries may differ. Parcellating a brain is a useful mechanism for analyzing neuroimaging data as it reduces complexity of the brain's activity to a finite number of domains, which can be assumed to play somewhat uniform functions.

Lack of precise parcellation information relating to a particular brain in question can, when surgery is performed, lead to collateral damage to brain functions, such as cognition. One can align an atlas (e.g., a set of three-dimensional (3D) points or voxels assigning voxels identity in a standard coordinate space to various parcellations) to the brain after warping it into a standard coordinate space, such as the Montreal Neurologic Institute (MNI) space. Pure anatomic-based techniques of atlasing can fail when applied to patients with structurally abnormal brains, such as those with brain tumors, stroke, hydrocephalus, traumatic brain injury and atrophy. For these and other reasons, there is a need to be able to map and visualize functional areas in individuals (e.g., in individuals with varying brains) in a way that addresses these issues, as it would make a number of valuable analytics possible to improve outcomes.

Brain graphs can be a useful way to display various structures and connectivity data amongst those structures in a brain. Since the brain graphs can include data associated with both lateral (non-deep) and deep structures, the brain graphs can become cluttered, thereby making it more challenging for a user to view particular areas or regions of interest in the brain. For example, the user may desire to view an insula. However, the insula can be buried beneath other structures, nodes, and/or edges in the brain graph. Sometimes, the user may not be able to separate the insula from the other structures, nodes, and/or edges, thereby hindering the user's ability to study and analyze the insula. Sometimes, the user can subset the brain graph, but isolating the insula using such a technique can make it challenging for the user to study the insula in context with other structures (both deep and non-deep), nodes, and edges in the brain.

The disclosed technology, therefore, provides one or more unique graphical user interfaces (GUIs) that can display relevant data of a brain over a representation of a brain (e.g., a glass brain, a two-dimensional (2D) brain, a three-dimensional (3D) brain, etc.). The relevant graph data can be displayed in such a way that allows users, such as medical professionals, to view different structures, nodes, and edges of the brain via different viewing settings. The structures in the brain can be labeled (e.g., labeled and annotated as lateral and deep structures) so that they can be more easily identified and viewed in different viewing settings presented in the GUIs. A medical professional can, for example, view all lateral and deep structures as well as their respective connectivity data (e.g., nodes and edges) in a particular patient's brain over the representation of a brain. Using various user-friendly selectable options in the GUIs, the medical professional can selectively view one or more of the lateral and/or deep structures relative to the other structures and connectivity data in the brain. The disclosed technology can provide for minimizing emphasis of certain foreground nodes and edges (e.g., lateral structures) to make it easier for the medical professional to focus on and analyze deeper structures that otherwise can be challenging to visualize and, consequently, understand.

For example, the medical professional can select an option to view the particular patient's insula. The representation of the brain can be updated to reflect the insula in a first brightness setting while all remaining, unselected portions of the brain (e.g., other deep structures, lateral structures, nodes, and edges, etc.) can be shaded and/or lowered in opacity (e.g., made more transparent). As a result, the medical professional can focus on the insula while also being able to analyze the insula in context, relative to other structures in the particular patient's brain. This can assist the medical professional to more clearly identify and analyze structures and connectivity amongst the structures in the particular patient's brain. Using this information, the medical professional can make more informed decisions about diagnosis, treatment, therapy, and medical procedures for the particular patient.

Sometimes, a medical procedure may include cutting into, puncturing, or otherwise excising portions of the brain that can impact various structures (e.g., hubs, parcellations, deep structures, lateral structures, etc.) and have long term cognitive effects on the particular patient. Medical professionals must be well informed about the structures and connectivity of such structures in the particular patient's brain to avoid detrimentally affecting the patient's cognitive abilities and making a mistake during the medical procedure. Since each patient can have different connectivity data, it is even more critical that the medical professional understand the particular patient's brain and consequences of their actions to avoid negatively impacting the particular patient during the medical procedure. The disclosed technology provides user-friendly, interactive GUIs that can be used by the medical professional to analyze the structures and connectivity data of a particular patient's brain before undergoing any medical procedure. Using the disclosed technology, the medical professional can view relationships between different structures (both lateral and deep) and plan what steps or actions can be taken during the medical procedure. The medical professional can therefore make more informed decisions regarding diagnosis, treatment, and/or medical procedures for the particular patient.

One or more embodiments described herein include a method including overlaying nodes representing locations of regions of a patient's brain on a representation of a brain, displaying the representation of the brain with the overlaid nodes in a graphical user interface (GUI), receiving user input indicating interest in focusing on one or more deep nodes, and taking an action based on the user input. The nodes can include deep nodes and non-deep nodes.

The embodiments described herein can optionally include one or more of the following features For example, the representation can be a representation of the brain in 2 dimensions (2D). The representation can also be a representation of the brain in 3 dimensions (3D).

As another example, the method can also include labeling the deep nodes as part of one or more deep brain structures. The deep brain structures can include at least one of a group of insula, lobes, and subcortical structures. In some implementations, the regions can include parcellations of the patient's brain.

As another example, taking an action based on the user input can include adjusting brightness settings of the one or more deep nodes of interest such that a brightness of the one or more deep nodes of interest exceeds a brightness of the overlaid nodes that the user input did not indicate interest in focusing on by a predetermined threshold. In some implementations, taking an action based on the user input can include displaying the overlaid nodes that the user input did not indicate interest in focusing on at an opacity level that is less than a second predetermined threshold. In yet some implementations, taking an action based on the user input can include adjusting brightness settings of the overlaid nodes that the user input did not indicate interest in focusing on such that the brightness of the overlaid nodes that the user input did not indicate interest in focusing on is less than the brightness of the one or more deep nodes of interest by the predetermined threshold.

In some implementations, the method can also include displaying first and second portions of the representation of the brain with the overlaid nodes, receiving user input indicating selection of one of the first and second portions of the representation of the brain, and in response to receiving the user input, removing the selected one of the first and second portions of the representation of the brain such that only the overlaid nodes in the selected one of the first and second portions of the representation of the brain are visible. In yet some implementations, the first portion of the representation of the brain can represent a right side of the patient's brain and the second portion of the representation of the brain can represent a left side of the patient's brain.

As another example, taking an action based on the user input can include displaying information about the one or more of the deep nodes of interest over a portion of the GUI.

As yet another example, taking an action based on the user input can include displaying information about the one or more of the deep nodes of interest in a second GUI.

One or more embodiments described herein can include a method including overlaying nodes representing locations of brain regions of a patient on a representation of a brain, displaying the representation of the brain with the overlaid nodes in a graphical user interface (GUI), receiving user input indicating interest in focusing on one or more nodes of interest, and taking an action based on the user input. The nodes can include at least nodes of interest.

The embodiments described herein can include one or more of the abovementioned features and one or more of the following features. For example, the nodes of interest can include deep nodes. The nodes can also include lateral nodes. As another example, the representation can be a representation of the brain in 3 dimensions (3D). The method can also include labeling the nodes of interest as part of one or more deep brain structures. In some implementations, the deep brain structures can include at least one of a group of insula, lobes, and subcortical structures. As another example, the brain regions can include parcellations of the patient's brain.

The subject matter described herein provides numerous advantages. For example, the disclosed technology can provide medical professionals with an interface that allows for gleaning insights about a brain. Present imaging systems can be cumbersome to use and operate, and typically can produce outputs that lack clinical usefulness. The disclosed technology, on the other hand, processes images of the brain and outputs them in an interactive, user-friendly graphical user interface (GUI) of a brain navigation system. The medical professional can then interact with portions of the particular brain in question using the GUI. As a result, the medical professional can glean more insight about the parcellations of the particular brain, which can be used to determine appropriate diagnoses, treatments, surgical procedures, and other research or clinical purposes that are specific to the particular brain in question.

Brain graphs can be difficult to study in a meaningful way, especially with regards to understanding relationships between lateral and deep structures in a particular patient's brain. A medical professional may study a brain graph to plan out a medical procedure. However, the brain graph can be so cluttered with data points that the medical professional may overlook or misinterpret one or more deep structures and their associated connectivity data. The medical professional may then perform steps in the medical procedure based on their misinterpretation of the deep structures, which can cause detrimental repercussions on the cognitive functionality of the particular patient. The disclosed technology, on the other hand, transforms brain graphs into interactive, user-friendly depictions of the brain in 3D space that can provide greater insight about the structures in the brain and connectivity data of those structures. As described throughout, the disclosed technology can depict both lateral and deep structures and provide the medical professional or other user with selectable options to view different structures in the brain relative to unselected structures in the brain. The medical professional can therefore have a more wholesome understanding and view of the selected structures as they relate to other structures in the brain. Since the medical professional can better understand and analyze relationships between different structures in the brain, the medical professional can improve their decision making process with regards to diagnosis, treatment, and medical procedures.

Improved and more accurate diagnosis, treatment, and medical procedures can also improve health and safety of the particular patient.

Moreover, connectivity data amongst nodes (both deep and lateral) can be visually represented in a variety of ways to further assist the medical professional's understanding and analysis of connectivity amongst both deep and lateral structures in the particular patient's brain. Colors, for example, can be used, to demonstrate different levels of connectivity between deep and lateral nodes (e.g., deep nodes can be represented in a first color and lateral nodes can be represented in a second color). When the medical professional selects particular nodes and/or portions of the brain (e.g., deep structures), the selected portions can be displayed in a first indicia while unselected portions of the brain can be displayed in a second indicia. The first indicia can be brighter settings and/or highest opacity while the second indicia can be darker settings and/or lower opacity (e.g., shading). As a result, the medical professional can visually focus on the selected portions of the brain while still viewing the selected portions relative to the unselected portions. The medical professional can therefore more accurately conceptualize and analyze relationships between different structures in the particular patient's brain to make more informed decisions with regards to diagnosis, treatment, and/or medical procedures for the particular patient.

As described throughout, the GUIs can also be designed to be user-friendly and intuitive to provide ease of use to any user, including but not limited to medical professionals and non-medical users (e.g., a patient, student, etc.). User-friendly functionality includes hovering over nodes or edges to view additional information about such features in the particular patient's brain, selecting portions of the brain to view additional information and/or to view the selected portions in different GUIs or windows, and/or selecting options to view labeled structures in the brain in an indicia that is different than unselected structures in the brain. One or more other user-friendly controls and functionality are possible, as described herein. The different, user-friendly views and functionality can be advantageous to assist the user in analyzing the particular patient's brain and making decisions about the particular patient's condition (e.g., diagnosis, treatment, medical procedure, drug therapy, etc.).

The disclosed technology can also provide ways to view highly complex brain data in a network. Therefore, the brain data can be more digestible for users. Since the disclosed technology can provide for synthesis and analysis of robust and complex sets of data pertaining to a particular patient's brain, a relevant user, such as a medical professional, can more appropriately and accurately diagnose the particular patient's condition and also apply the data to different types of analyses.

The details of one or more variations of the subject matter described herein are set forth in the accompanying drawings and the description below. Other features and advantages of the subject matter described herein will be apparent from the description, drawings, and claims.

BRIEF DESCRIPTION OF DRAWINGS

Like reference symbols in various drawings indicate like elements.

DETAILED DESCRIPTION

This document generally relates to providing interactive GUIs for users, such as medical professionals, to glean insight about connectivity data associated with a particular brain. Using the GUIs, for example, a medical professional can more accurately tailor diagnosis, treatment, and/or procedures for a particular patient and their condition. Using the disclosed technology, imaging data of a brain can, for example, be overlaid on a glass brain or some other representation of a generic brain. The modelled version of the brain can be outputted in a GUI or other user interface display at a user device. The medical professional can then interact with the modelled version of the brain in order to make more informed decisions about the particular patient's condition. Although this disclosure is described from a perspective of a medical professional, the disclosed technologies can be used by any other type of user, including but not limited to clinicians, doctors, nurses, patients, researchers, professors, scientists, students, or other users that may not be trained to study the brain. Moreover, although this disclosure is described in relation to patient brains, the disclosed technologies can also be used in relation to human and other species brains.

As described herein, the medical professional can interact with the modelled version of the brain in order to more easily and intuitively analyze particular deep and/or lateral structures in the patient's brain. The medical professional can use their analysis to make more informed decisions about how to address the patient's condition. For example, the medical professional can select options to view one or more deep structures in the particular patient's brain. By selecting such options, the deep structures can be depicted in a first indicia and unselected structures can be depicted in a second indicia, such as a shading. The medical professional can therefore focus on the deep structures while being able to view such structures relative to the unselected structures. The medical professional can therefore make more informed decisions about the deep structures. The medical professional can also hover over nodes (e.g., deep and/or lateral) and/or edges of the modelled brain to view additional information about those areas of interest. This additional information can be used by the medical professional to make more informed decisions about the particular patient's condition. Sometimes, the medical professional can also highlight or select areas in the brain that the medical professional may excise during a medical procedure. The modelled version of the brain can be updated to reflect repercussions of performing such an excision on other portions of the brain. The updated brain can be advantageous to assist the medical professional in assessing the consequences of actions that may be taken during a medical procedure.

Figure 1:
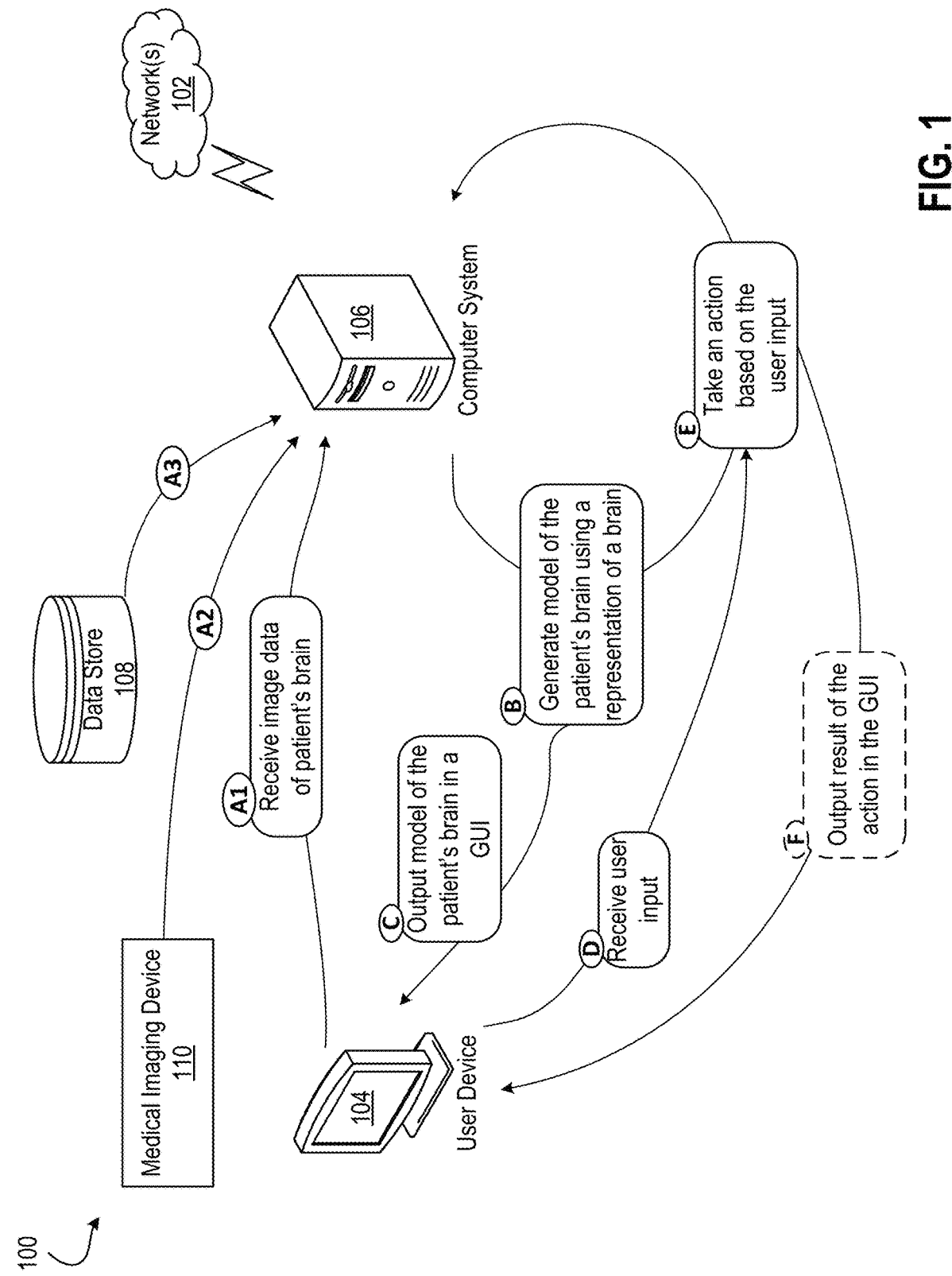
FIG. 1 is a conceptual diagram illustrating a computing environment for generating a GUI representation of a particular brain.

Referring to the figures, FIG. 1 is a conceptual diagram illustrating a computing environment 100 for generating a GUI representation of a particular brain. The computing environment 100 can include a user device 104, a computer system 106, a data store 108, and a medical imaging device 110, which can communicate (e.g., wired and/or wirelessly) via network(s) 102.

The user device 104 can be used by a medical professional, such as a clinician, surgeon, doctor, nurse, researcher, or other professional. The user device 104 and technologies described herein can be used by any other user. The user device 104 can be any one of a computer, laptop, tablet, mobile device, mobile phone, and/or smartphone. Sometimes, the user device 104 can be integrated into or otherwise part of one or more other devices in a medical setting, such as the medical imaging device 110 and/or the computer system 106. The medical professional can use the user device 104 to view information about a patient's brain. For example, using the disclosed technology, the medical professional can view, at the user device 104, 3D representations of a particular patient's brain and make determinations about what diagnosis, treatment, and/or surgical procedures to perform. The medical professional can also view other/ additional information about the particular patient at the user device 104 to make more informed decisions with regards to the particular patient's diagnosis, treatment, surgery, or other medical or research purposes. Thus, the user device 104 can provide hardware that can support the GUIs, software, and applications described herein, such as a singular and interactive brain navigation system that makes it easier and more intuitive for the medical professionals to make medical and research determinations.

The computer system 106 can be a remote computing system, a cloud-based system or service, and/or integrated with or otherwise part of one or more devices in a medical setting (e.g., such as the user device 104 and/or the medical imaging device 110). The computer system 106 can be a computer, processor, a network of computers, a server, and/or a network of servers. Sometimes, each medical setting (e.g. a hospital) can have one or more computer systems 106. Sometimes, the computer system 106 can be used across multiple medical settings (e.g., multiple hospitals). The computer system 106 can be configured to generate interactive representations of patients' brains based off image data of the brains. The computer system 106 can also generate GUIs to display the interactive representations of the brains at the user device 104.

Sometimes, the computer system 106 can clean the image data by removing personally identifying information (e.g., protected health information (PHI)) from that data. Cleaning the image data can be beneficial to preserve patient privacy, especially if the interactive representations of patients' brains are used for medical research, clinical studies, or otherwise are stored in the data store 108 for future retrieval and use. Removing personally identifying information can also be advantageous if the computer system 106 is remote from the user device 104 and the interactive representations of the brain are generated at the computer system 106 that is outside a secure hospital infrastructure or other network where the image data may be generated and/or the interactive representations of the brain may be outputted. In other words, removing personally identifying information can be advantageous to preserve patient privacy when patient data is communicated between different networks and/or infrastructure.

The data store 108 can be a remote data store, cloud-based, or integrated into or otherwise part of one or more other components in the medical setting (e.g., such as the user device 104 and/or the computer system 106). The data store 108 can store different types of information, including but not limited to image data of patient brains (e.g., from the medical imaging device 110), cleaned image data (e.g., from the computer system 106), 3D representations of patient brains or other interactive representations of patient brains (e.g., from the computer system 106), connectivity data associated with patient brains, determinations, actions, or other user input taken by the medical professional (e.g., at the user device 104), patient information or records, or other relevant information that can be used in a medical setting.

The medical imaging device 110 can be any type of device and/or system that is used in the medical setting to capture image data of patient brains. The medical imaging device 110 can capture image data that includes but is not limited to x-rays, computed tomography (CT) scans, magnetic resonance imaging (MRIs), and/or ultrasound. One or more other types of image data can also be captured by the medical imaging device 110. The computer system 106 can be configured to receive any type of image data of a patient's brain and glean connectivity data about the brain from that image data to map the data onto a user-friendly interactive representation of a brain.

Still referring to FIG. 1, the computer system 106 can receive image data of a patient's brain from one or more of the user device 104 (step A1), the medical imaging device 110 (step A2), and the data store 108 (step A3). Sometimes, for example, when the user device 104 is part of the medical imaging device 110, the computer system can receive the image data captured by the medical imaging device 110 from only one device (e.g., the medical imaging device 110 or the user device 104). The image data can be captured by the medical imaging device 110 then sent directly, in real-time, to the computer system 106 (step A2) for real-time processing. Sometimes, the image data can be captured by the medical imaging device 110, then initially reviewed by the medical professional at the user device 104. Accordingly, the user device 104 can transmit the image data to the computer system 106 (step A1).

In some implementations, image data can be captured of multiple different brains by multiple different medical imaging devices 110. The image data can be stored in the data store 108 for future processing and analysis. The computer system 106 can then retrieve a batch or batches of the image data from the data store 108 (step A3) and process the image data in batch. Processing in batch can be advantageous to use fewer computational resources and reduce network bandwidth.

Once the computer system 106 receives the image data (steps A1-A3), the computer system can generate a model of the brain using a representation of a brain (step B). For example, the computer system 106 can map or model the patient's brain from the image data onto a 3D representation of a brain. The 3D representation can be a generic brain in 3-dimensional or other multi-dimensional space. The 3D representation can be a glass brain. Mapping the patient's brain onto the glass brain can be advantageous to provide vantage points of different structures, parcellations, and connectivity in the particular patient's brain. A medical professional can more easily analyze the particular patient's brain via the 3D representation of the brain rather than through the raw image data captured by the medical imaging device 110. As a result, the medical professional can generate more informed decisions and determinations with regards to the particular patient's diagnosis, treatment, surgery, condition, or other medical or research purposes.

Once the patient's brain is modeled using the representation of the brain (step B), the computer system 106 can output the model of the patient's brain in a GUI at the user device 104 (step C). For example, the computer system 106 can generate the GUI that displays the model of the patient's brain, then transmit the GUI to the user device 104 to be outputted. The model can represent the patient's brain overlaid on the glass brain. Sometimes, instead of outputting the model at the user device 104 (step C), the computer system 106 can store the model of the patient's brain in the data store 108. The model of the patient's brain can then be accessed/retrieved at a later time and presented to the medical professional or other user at the user device 104.

As mentioned throughout, when the model of the patient's brain is outputted at the user device 104, the GUI can allow the medical professional to take numerous actions in response to reviewing the model of the patient's brain. For example, the medical professional can determine what type of diagnosis, treatment, or surgical procedures to take with regards to this particular patient. The medical professional can also interact with the model of the patient's brain through use-selectable options and features in the GUI that is outputted at the user device 104. The medical professional can change views of the model of the patient's brain (e.g., rotate around the model, view only a left or right side of the patient's brain, etc.), select portions of the patient's brain from the model (e.g., select a particular lobe, node, parcellation, etc.), view other information about the patient (e.g., health records, prior medical visits, etc.), and simulate surgical procedures that can impact different parcellations or portions of the patient's brain (e.g., slicing a node or nodes that are connected to other nodes in the patient's brain). The medical professional can provide input to the user device 104, for example, via an input device, and the input can indicate the medical professional's interaction(s) with the model of the patient's brain. This input can then be received by the computer system 106 (step D).

The computer system 106 can take an action based on the received user input (step E). For example, if the medical professional changes or selects a different view of the model of the patient's brain, then the computer system 106 can generate an updated GUI display of the patient's brain that only includes the selected view. This updated GUI display can be outputted at the user device (step F). As another example, the medical professional can remove one or more nodes from the model of the patient's brain. The computer system 106 can receive this input (step D), simulate removal of the user-selected nodes (step E), then output results of removing such nodes from the brain at the user device 104 (step F). The medical professional can review the outputted results and take further actions in response. Further actions can include decisions about what nodes the medical professional should remove during the actual medical procedure and/or how to proceed with diagnosis, treatment, and/or the medical procedure.

Sometimes, the computer system 106 can take an action based on the user input (step E) that does not also include outputting a result of the action at the user device 104 (step F). For example, the medical professional can input notes about what actions the medical professional intends to take during a medical procedure, a diagnosis for the particular patient, and/or treatment for the patient. The computer system 106 can receive this input and store it in the data store 108 but may not output results from storing this input. This input can then be retrieved from the data store 108 and provided to one or more other devices (e.g., a report can be generated that indicates the patient's diagnosis and treatment). The report can then be provided to a device of the patient. The report can also be transmitted to devices of other medical professionals, such as those in a hospital infrastructure/network). The computer system 106 can take one or more other actions based on the user input (step E) and optionally output results of the action(s) at the user device 104 (step F).

Figure 2:
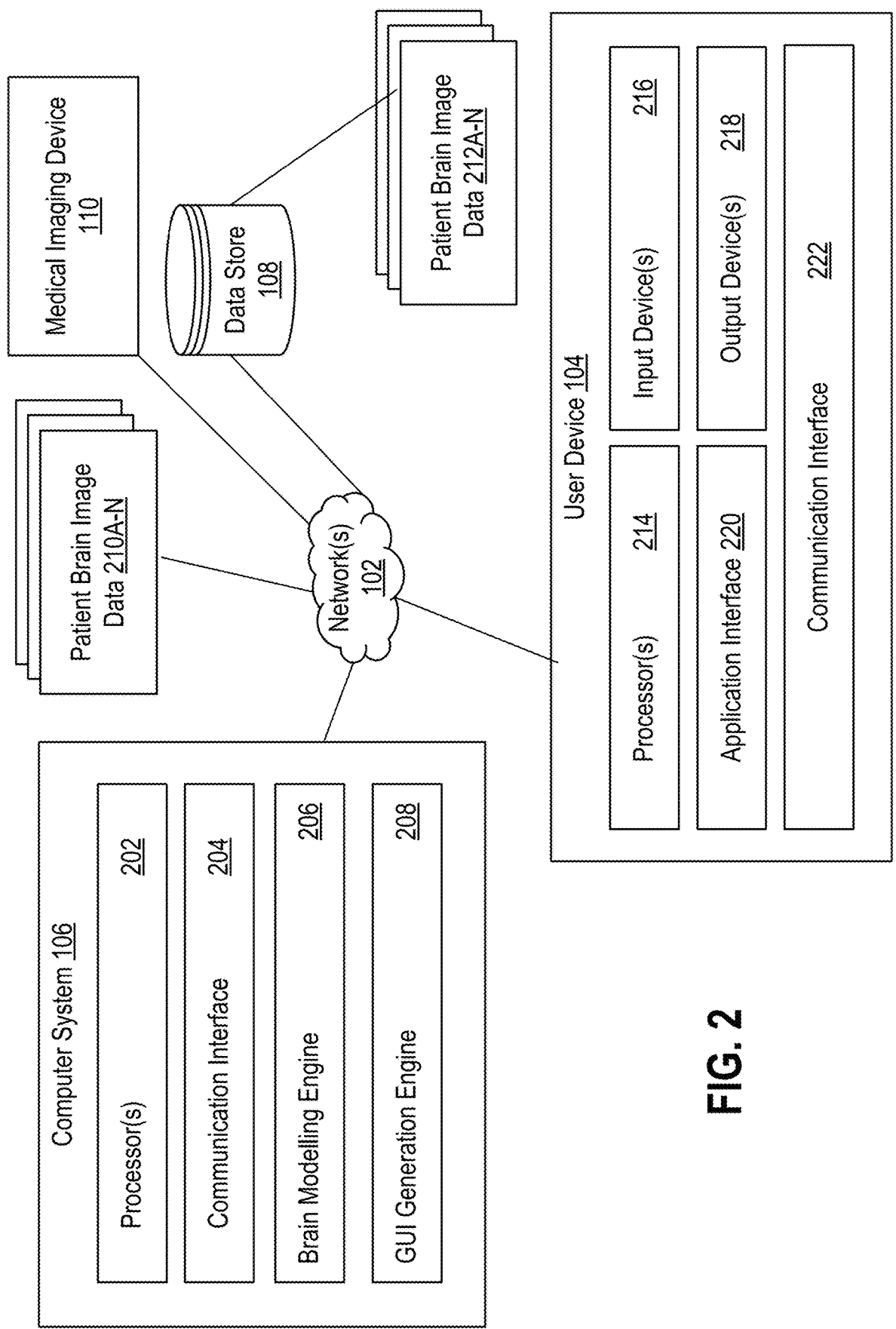
FIG. 2 illustrates components in a computing landscape that can be used to generate the GUI representation of the particular brain.

FIG. 2 illustrates components in a computing landscape that can be used to generate the GUI representation of the particular brain. As described above, the user device 104, computer system 106, data store 108, and medical imaging device 110 can communicate via the network(s) 102. One or more of the components 104, 106, 108, and 110 can also be integrated into a same computing system, network of devices, server, cloud-based service, etc. The network(s) 102 may be a wide-area network (WAN), such as the Internet, a cellular telecommunications network, or a private WAN. Connection via the network(s) 102 can include a traditional dial-up modem, a high-capacity (e.g., cable) connection such as a broadband modem, and/or a wireless modem.

The computer system 106 can include processor(s) 202, communication interface 204, brain modelling engine 206, and GUI generation engine 208. The processor(s) 202 can be configured to perform one or more operations described herein. Although not depicted, the computer system 106 can also include at least one memory unit, which may have semiconductor random access memory (RAM) and semiconductor read only memory (ROM).

One or more of the techniques and processes described herein can be implemented as software application programs executable by the processor(s) 202 in the computer system 106. Moreover, one or more of the techniques and processes described herein can be executed in browsers at remote terminals, systems, or devices (e.g., the user device 104 and/or another computer system), thereby enabling a user of the remote terminals, systems, or devices to access the software application programs that are executing on the computer system 106. For example, steps for any of the techniques and processes described herein can be effected by instructions in the software application programs that are carried out within the computer system 106. Software instructions may be formed as one or more code modules (e.g., using PYTHON or equivalent language modules installed on the computer system 106 and/or the remote terminals, systems, or devices), each for performing one or more particular tasks. The software instructions can also be divided into separate parts. For example, a first part and the corresponding code module(s) can perform the techniques and processes described herein and a second part and the corresponding code module(s) can manage a user interface (e.g., the GUIs described herein) between the first part and the medical professional at the user device 104.

Moreover, the software may be stored in a non-transitory, tangible, computer readable medium, including storage devices described throughout this disclosure. The software can be loaded into the computer system 106 from the computer readable medium, and then executed by the computer system 106. A computer readable medium having such software or computer program recorded on the computer readable medium can be a computer program product. Examples of transitory or non-tangible computer readable transmission media that may also participate in the provision of software, application programs, instructions and/or data include radio or infra-red transmission channels as well as a network connection to another computer or networked device, and the Internet or Intranets, including e-mail transmissions and information recorded on Web sites and the like.

Still referring to the computer system 106, the brain modelling engine 206 can be configured to map a patient's brain onto a representation of a brain (e.g., refer to step B in FIG. 1). For example, the brain modelling engine 206 can receive patient brain image data 210A-N, which can be used to generate a model of the patient's brain. The patient brain image data 210A-N can be received from the medical imaging device 110. The patient brain image data 210A-N can also be received from the user device 104. In some implementations, as described in reference to FIG. 1, the computer system 106 can retrieve patient brain image data 212A-N from the data store 108. The patient brain image data 212A-N can then be used by the brain modelling engine 206 to model the patient's brain.

Sometimes, modelling the brain can include identifying connectivity data for the particular brain. Modelling the brain can then include mapping the connectivity data over the representation of a generic brain. In yet some implementations, modelling the patient's brain can include identifying hubs, parcellations, deep nodes, lateral nodes, and other portions of the patient's brain that can be mapped onto the representation of the generic brain. Moreover, the brain modelling engine 206 can be configured to identify personally identifying information in the image data of the brain and extract that information before mapping the patient's brain onto the representation of the generic brain. The brain modelling engine 206 can use one or more machine learning models to accurately map the particular patient's brain data onto a representation of the generic brain.

In some implementations, for example, Digital Imaging and Communications in Medicine (DICOM) images of a particular brain to be parcellated can be processed by the brain modelling engine 206. DICOM is an international standard for transmitting, storing, retrieving, processing and/or displaying medical imaging information. A registration function for the particular brain can be determined in a Montreal Neurological Institute (MNI) space (a common coordinate space) described by a set of standard brain data image sets, a registered atlas from a human connectome project can be determined, and diffusion tractography of the DICOM images can be performed to determine a set of whole brain tractography images of the particular brain (in neuroscience, tractography can be thought of as a 3D modelling technique used to represent white matter tracts visually). For each voxel in a particular parcellation in the registered atlas, voxel level tractography vectors showing connectivity of the voxel with voxels in other parcellations can be determined, the voxel can be classified based on the probability of the voxel being part of the particular parcellation, and determining of the voxel level tractography vectors and the classifying of the voxels for all parcellations of the HCP-MMP1 Atlas can be repeated to form a personalised brain atlas (PBs Atlas) containing an adjusted parcellation scheme reflecting the particular brain.

The GUI generation engine 208 can be configured to generate GUI displays of the modelled brain. The GUI generation engine 208 can receive the modelled brain from the brain modelling engine 206 and generate an appropriate GUI for displaying the modelled brain to the medical professional (e.g., refer to FIG. 3). The GUI generation engine 208 can also transmit the generated GUI(s) to the user device 104 to be outputted/presented to the medical professional.

Moreover, whenever user input is received from the user device 104 that includes performing some action in response to the outputted model of the brain, the input can be received by the computer system 106. The brain modelling engine 206 can take some action (e.g., refer to step E in FIG. 1) in response to receiving the user input (e.g., refer to step D in FIG. 1). That action can include, for example, simulating removal of one or more nodes in the patient's brain. The GUI generation engine 208 can generate updated GUI displays based on the actions taken by the brain modelling engine 206 (e.g., refer to step F in FIG. 1). The GUI generation engine 208 can then transmit the updated GUI displays to the user device 104 to be outputted to the medical professional.

Sometimes, one or more of the components of the computer system 106, such as the brain modelling engine 206 and the GUI generation engine 208 can be part of one or more different systems. For example, the brain modelling engine 206 can be part of a software application program that can be loaded and/or executed at another device, such as the user device 104 and/or the medical imaging device 106. As another example, the GUI generation engine 208 can be part of a software application program that is executed at the user device 104 and the brain modelling engine 206 can be executed at the computer system 106 or another remote computing system, server, or cloud-based server or system.

The user device 104 can include processor(s) 214, input device(s) 216, output device(s) 218, application interface 220, and communication interface 222. The processor(s) 214 can be configured to perform one or more operations described herein. Although not depicted, the user device 104 can also include at least one memory unit, which may have semiconductor random access memory (RAM) and semiconductor read only memory (ROM).

The input device(s) 216 and output device(s) 218 can include one or more of an audio-video interface that couples to a video display, speakers, and/or a microphone, keyboard, mouse, scanner, camera, touch screen display, other display screen(s) (e.g., LCDs), joystick, and/or other human interface device. The input device(s) 216 can be configured to receive user input from the medical professional or other user. The output device(s) 218 can be configured to output the model of the patient's brain and/or actions taken by the computer system 106 in response to the user input. The output device(s) 218 can present a variety of GUI displays and information to the medical professional, where such displays and information are generated by the computer system 106. The output device(s) 218 can also output information that is received or otherwise generated by the medical imaging device 110.

The application interface 220 can be executable software or another program that is deployed at the user device 104. The GUIs generated by the computer system 106 can be displayed or otherwise outputted via the application interface 220. In some implementations, the application interface 220 can be executed at a browser of the user device 104. The medical professional can then access and view the GUIs via the Internet or other connection. Sometimes, the application interface 220 can be executed as a software module/program/product at the user device 104. The application interface 220 can provide the interactive GUIs to the medical professional and receive input from the medical professional (e.g., refer to FIG. 3).

The communication interfaces 204 and 222 can be configured to provide communication between and amongst the components described herein. For example, a modem can be integrated therein.

Figure 3:
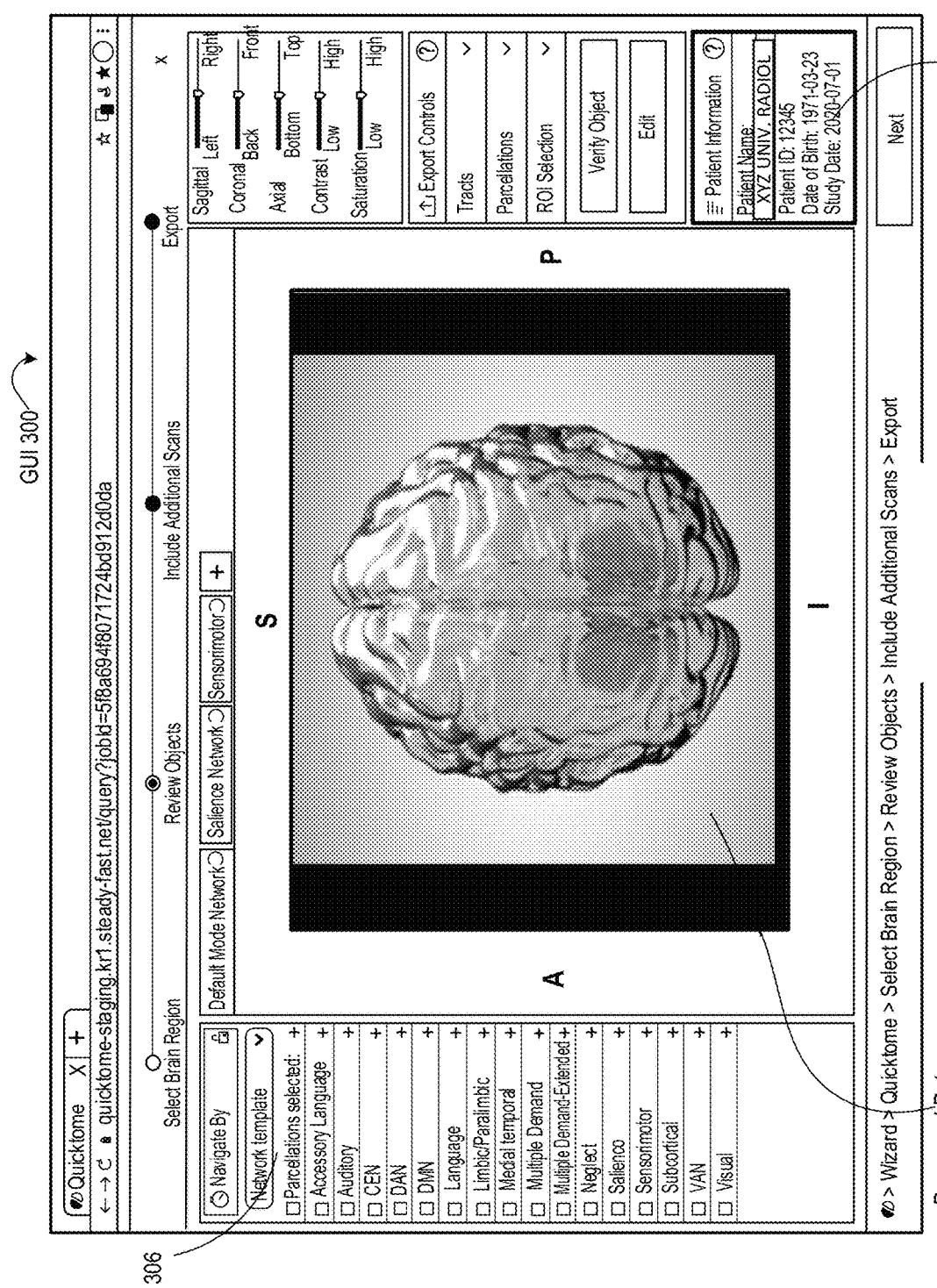
FIG. 3 illustrates a user-interactive GUI display of the particular brain.

FIG. 3 illustrates a user-interactive GUI 300 of the particular brain. The GUI 300 can be outputted at the user device 104 described herein. The GUI 300 outputs processed medical imaging data that is received of the particular brain. For example, the GUI 300 can include processed data 302, patient information 304, and selectable options 306. The processed data 302 can include the particular brain as it is modeled on a representation of a brain. For example, the processed data 302 can include a 3D representation of the particular brain, such as the particular brain overlaying a glass brain. The processed data 302 also may not include other information that can appear in imaging data, such as patient information or other PHI. The PHI that corresponds to the processed data 302 can optionally be outputted in the patient information 304.

The GUI 300 can provide a brain navigation system that is configured to display visual representations of an interior of the particular brain for clinical analysis and medical intervention, as well as visual representation of physiology of specific portions or objects of the brain (e.g. tracts, hubs, or parcellations of the brain). Such visual representations can reveal internal structures hidden by the skin and bones, and can be used to diagnose and treat various different diseases.

The medical professional can use the selectable options 306 to specify particular actions (e.g. by making selections in the GUI 300 presented at the user device 104) that the medical professional would like to take with regards to the processed data 302. The medical professional can also choose options to export the processed data within an IT network of the hospital or other medical setting where the medical professional works. The medical professional can save the exported data (e.g., in the data store 108 in FIG. 1), which can be used in future research and analysis.

The GUI 300 presents only some options that may be presented to the medical professional with regards to the processed data 302. One or more other options are also possible and can be presented in the GUI 300 and/or in additional GUIs that are outputted at the user device 104.

Moreover, as described herein, the GUI 300 can be part of a specialized computing system in the hospital IT infrastructure. Sometimes, the GUI 300 can also be accessible via a web browser. The GUI 300 may be configured—e.g. by authentication mechanisms such as login using username and/or password, biometric detection, and/or the like-to be used by only authorized individuals, such as clinicians (e.g. doctors, nurses, clinical staff, or the like), other medical professionals, or other authorized users (e.g. network administrator, technical staff, or the like) at the hospital or other medical setting. In some implementations, the GUI 300 can also be in communication with or otherwise linked to one or more external devices, such as remote computers, that can be used to facilitate brain surgery or other medical procedures.

Although a brain image is useful for a medical professional, the medical professional can benefit more if they have additional information about components of the brain that is imaged. This additional information can be advantageous for the medical professional to make more informed decisions with regard to diagnosis, treatment, and medical procedures. Accordingly, as shown in FIG. 3, the GUI 300 can provide the medical professional with tools (e.g., such as the selectable options 306) that allow the medical professional to interact with the modelled version of the particular brain. The medical professional can provide input for selecting portions of the processed data 302. The selected portions can be objects—e.g. brain tracts and/or brain parcellations—that the medical professional desires to see more information about, remove from the brain in a simulated procedure, or otherwise review and analyze. Accordingly, the medical professional can specify particular portions of the brain to analyze. The medical professional may also desire to identify and specify, on the GUI 300, particular objects on several features, such as local properties of brain tissue, long-range connectivity patterns, structural markers, functional markers, and/or the like. The disclosed technology therefore can provide the medical professional with a more comprehensive, interactive, and user friendly interface for making determinations about a particular patient's brain condition(s).

Figure 4A:
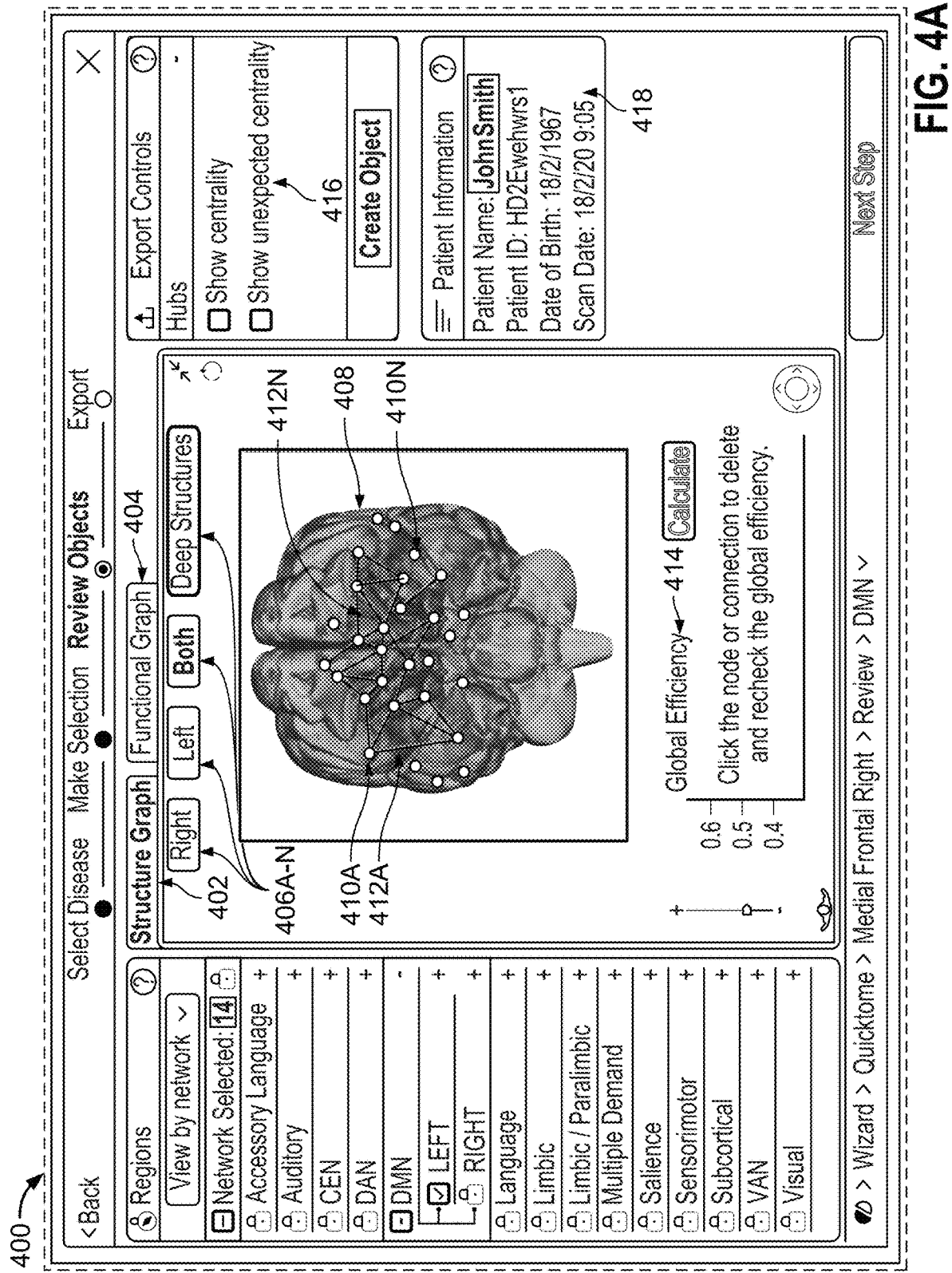
FIGS. 4A-C depict example GUI displays of the particular brain and deep structures therein.
Figure 4B:
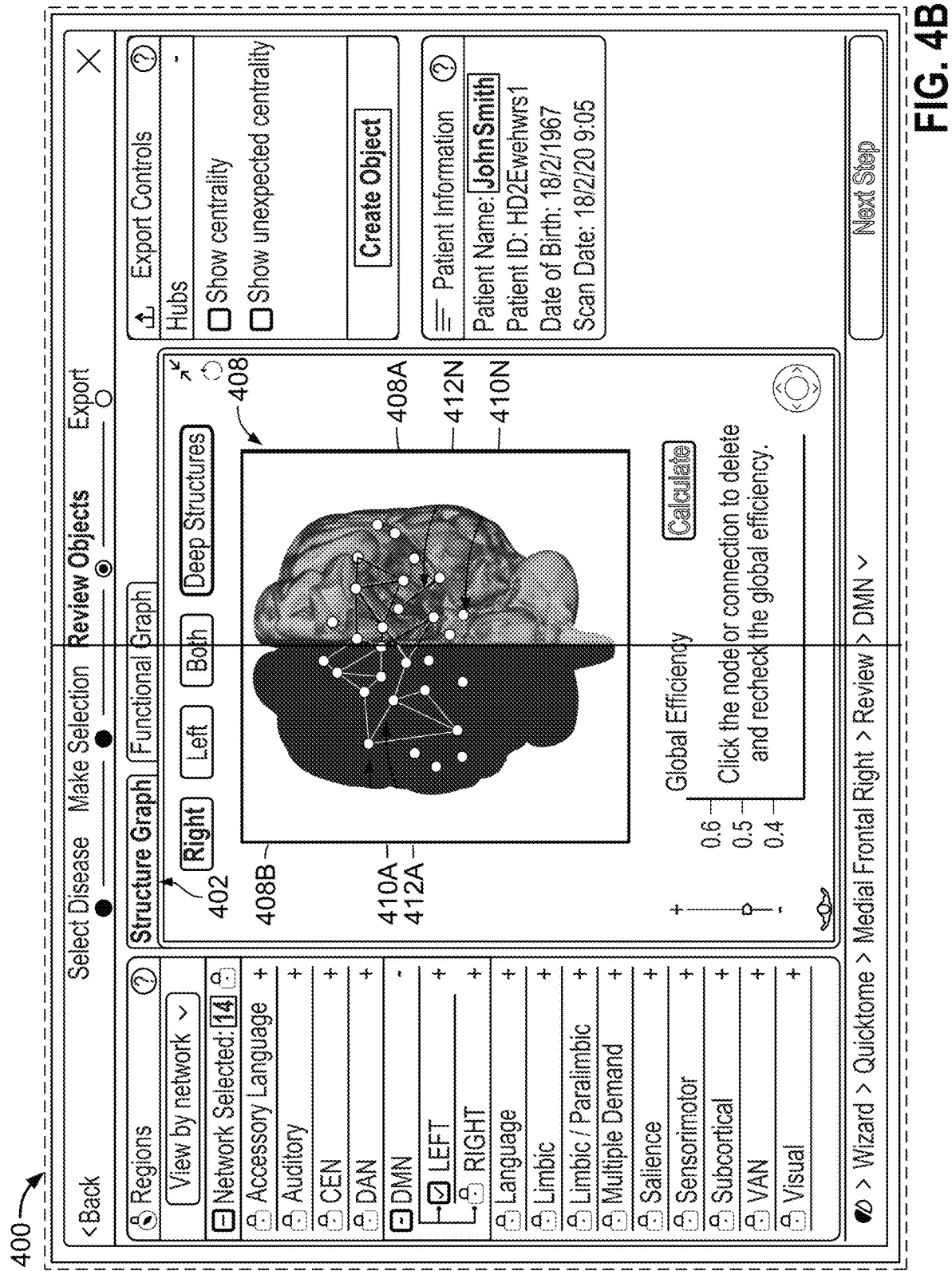
Figure 4C:
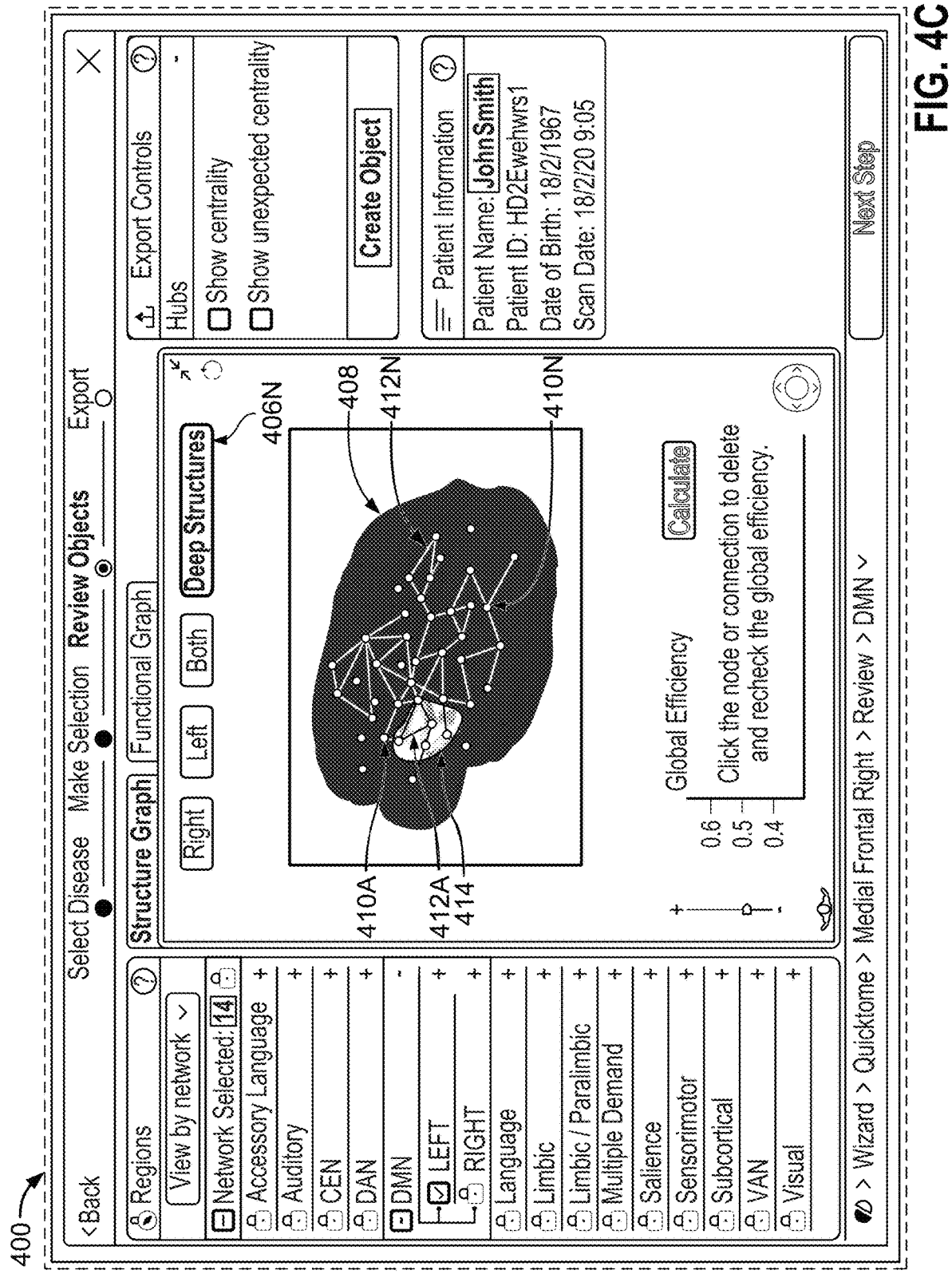

FIGS. 4A-C depict example GUI displays 400 of the particular brain and deep structures therein. Referring to FIG. 4A, GUI 400 is presented at a user device (e.g., the user device 104 in FIGS. 1-2) for display to the medical professional or other relevant user. The GUI 400 includes several selectable options, panels, and/or windows that can be used by the medical professional to customize their interaction with and analysis of the particular brain. The GUI 400 can be part of a suite of GUIs in a software package or application. The software package or application can include various functionality to study brain data. For example, the software package or application can include GUIs that provide functionality to view different aspects of the brain (e.g., hubs, unexpected hubs, connectivity data, etc.) and/or to simulate surgical or other medical procedures. The software package or application can include additional functionality.

The GUI 400 can be used in a clinical setting (e.g., during diagnosis and treatment of a particular patient) and/or in a research setting (e.g., during population analysis/studies). Moreover, as described throughout, the GUI 400 can be used in other settings and by other users, not just medical professionals.

The GUI 400 can have selectable options for a structure graph 402 and a functional graph 404. In FIG. 4A, the structure graph 402 has been selected. As a result, a patient's brain can overlay a glass brain 408 (e.g., a generic representation of a brain). Connectivity data associated with the particular patient's brain can be mapped onto the glass brain 408. The connectivity data can represent different nodes and edges in the patient's brain. Such nodes and edges can also be defined for particular structures in the patient's brain, including both deep and lateral structures. In some implementations, a node can represent a functional region (e.g., a parcellation) and a value of an edge can represent a degree of connectivity between two nodes where connectivity can be measured by, for example, number of tracts, correlation of functional activity, or a combination of both. Accordingly, the glass brain 408 can be overlaid with nodes and edges that correspond to both deep and lateral structures.

In some implementations, different types of brain graphs or representations of a brain can be used (e.g., 2D representation of the brain, 3D representation of the brain, etc.). Whereas the structure graph 402 can illustrate a number of fibers in the particular patient's brain, the functional graph 404, although not depicted, can be a connectivity matrix of the particular patient's brain, thereby demonstrating correlations between different deep and lateral structures in the particular patient's brain (e.g., such as parcellations, hubs, or other portions of the brain). In some implementations, the structure graph 402 can be preferred for neurosurgery purposes while the functional graph 404 can be preferred for research-type analyses.

The GUI 400 can also present selectable options 406A-N to view different portions of the particular patient's brain on the glass brain 408. When the medical professional or other user selects one of the options 406A-N, the glass brain 408 can be automatically updated and displayed in the same GUI 400. In some implementations, upon selection of one of the options 406A-N, the glass brain 408 can be updated and displayed in another or separate window and/or GUI. The options 406A-N include viewing a right side of the brain, a left side of the brain, both sides of the brain, and deep structures of the brain. One or more other options can also be presented to the medical professional, such as options to view particular structures in the brain. As an illustrative example, another option can be presented on the GUI 400 to view the insula of the brain. As yet another illustrative example, another option can be presented on the GUI 400 to view only lateral structures of the brain.

By selecting one of the options 406A-N, the GUI 400 can be updated to reflect just the portion of the brain that has been selected. Sometimes, the GUI 400 can be updated to reflect the portion of the brain that has been selected in a first indicia and portions of the brain that were not selected in a second indicia. The first indicia, for example, can be a brighter setting (e.g., brightest setting(s)) or opacity (e.g., 100% opacity). The second indicia, for example, can be a darker setting (e.g., greyed out, shaded) or lower opacity (e.g., less than 50% opacity or less than some predetermined threshold opacity level/amount).

As an example, the medical professional may select the option to view the right side of the brain. The right side of the brain can be depicted in the GUI 400 in a brightest light setting and opacity. Nodes, edges, and structures of the right side of the brain, including both lateral and deep structures, can be depicted at full brightness, color, and opacity. The left side of the brain can still be depicted in the GUI 400, but in lower light settings and opacity such that the left side of the brain is less visible. Nodes, edges, and structures of the left side of the brain can be shaded, in black and white or other monochromatic features, and/or more transparent. Although the left side of the brain is less visible, the medical professional or other user can still view connectivity between nodes, edges, and structures in the right side of the brain with nodes, edges, and structures in the left side of the brain. As a result, the medical professional can have a more wholesome understanding and analysis of the particular patient's brain anatomy.

Such a display can be advantageous to show relativity and context between structures, nodes, and edges on both sides of the particular patient's brain with emphasis on the user-selected portion of the brain (e.g., in the above example, the selected portion is the right side of the brain). After all, removing visualizations of one side of the brain can make it more challenging for the medical professional to understand how midline structures can cross over into both sides of the brain and how nodes on one side of the brain may be connected to nodes on the other side of the brain. The disclosed technology therefore provides for improved visualizations that make it easier for the medical professional to understand deep and lateral structures in context to make more informed decisions about diagnosis, treatment, and/or medical procedures for the particular patient.

In FIG. 4A, the medical professional has selected the option to view both sides of the brain. Thus, the entire glass brain 408 is depicted with connectivity data of the particular patient's brain overlaid thereon. Full color, brightness, and opacity is used to depict the nodes, edges, and structures (both lateral and deep) in both sides of the particular patient's brain. The option to view both sides of the brain can be a default view of any patient's brain when the GUI 400 is executed and/or the particular patient's brain data is initially mapped onto the glass brain 408. The medical professional can then select the options 406A-N to customize their view of the particular patient's brain data on the glass brain 408.

Nodes 410A-N are depicted on top of (e.g., overlaid on) the glass brain 408. A computer system (e.g., the computer system 106 in FIGS. 1-2) can overlay the nodes 410A-N on the glass brain 408 using connectivity data in a brain graph (and/or brain image data). The nodes 410A-N can be both deep and lateral nodes, which are specific to the particular patient. After all, each patient can have different connectivity data. As described above, a default setting for the GUI 400 can be displaying all the nodes 410A-N on the glass brain 408. Sometimes, only some or a portion of the nodes 410A-N in the particular patient's brain can be overlaid on the glass brain 408. For example, only deep nodes may be overlaid on the glass brain 408. As another example, only lateral nodes may be overlaid on the glass brain 408. The medical professional can sometimes select which of the nodes 410A-N should be overlaid on the glass brain 408.

The nodes 410A-N are connected via edges 412A-N, which represent fibers in the particular patient's brain. As shown in the GUI 400 of FIG. 4A, some of the nodes 410A-N, such as node 410A, are connected to other nodes by the edges 412A-N. Other nodes, such as node 410N, may not be connected to other nodes. Nodes that are connected by edges can have higher connectivity than nodes that are not connected to other nodes. Moreover, nodes that are connected to many other nodes can have higher connectivity than nodes that are connected to fewer nodes.

As shown in FIG. 4A, the nodes 410A-N can be depicted in one or more indicia (e.g., circles, a first color) and the edges 412A-N can be depicted in one or more other indicia (e.g., circles, a second color). Different indicia can be selected and used to differentiate features in the particular patient's brain. The different indicia can improve ease of use and interaction with the GUI 400. In some implementations, deep nodes can be depicted in a first color while lateral nodes can be depicted in a second color. Sometimes, edges between deep nodes can be depicted in a first color and/or pattern, edges between deep nodes and lateral nodes can be depicted in a second color and/or pattern, and edges between lateral nodes can be depicted in a third color and/or pattern. Sometimes, all edges can be depicted in a first color and/or pattern and all nodes can be depicted in a second color and/or pattern. In some implementations, different structures in the brain can be depicted in different indicia. For example, the insula can be depicted in a first color, lobes can be depicted in a second color (or multiple colors), and subcortical structures can be depicted in a third color (or multiple colors). One or more other indicia besides color, patterns, and/or shapes can be used to visually depict features of the brain in a user-friendly and intuitive way. As an illustrative example, 3D surfaces and/or shapes can be generated from a combination of MRI data and a brain atlas (which is similar to a glass brain but for internal structures) and used to augment a depiction of the brain that is presented in the GUI 400.

Although the glass brain 408 is shown from one perspective in the GUI 400, the medical professional can also manually change the perspective of the glass brain 408. For example, the medical professional can zoom in and out on the glass brain 408 (e.g., by scrolling with a mouse, selecting zoom buttons or other options that are presented in the GUI 400, using keys on a keyboard, using some other input device, etc.). Zooming in and out can change what nodes and/or edges are displayed and/or how such nodes and/or edges are displayed. For example, when the medical professional zooms in, they can focus on deep structures and non-deep structures can automatically become displayed in darker settings or shading (e.g., transparency is increased to a predetermined threshold level, brightness is decreased to a predetermined threshold level, etc.). For example, the non-deep structures can automatically be displayed at a brightness setting that is 50% less than a brightness setting of the deep structures. The medical professional can also rotate a desired amount around the glass brain 408 (e.g., by clicking with a mouse on the GUI 400 and dragging the cursor left, right, up, and down, selecting rotation buttons or other options that are presented in the GUI 400, by using keys on a keyboard, using some other input device, etc.). Ability to change the perspective of the glass brain can improve user functionality, thereby making it easier and more intuitive for the medical professional to view different regions of interest in the particular patient's brain and to further analyze data associated with the regions of interest.

Still referring to FIG. 4A, the GUI 400 can output global efficiency metrics 414. The global efficiency metrics 414 can be used by the medical professional to determine what impact removing the selected node 410A-N or edge 412A-N may have on other connectivity data, structures (both deep and lateral structures), and/or cognitive functions of the particular patient. For example, the computer system 106 described herein can calculate and determine reasonable parcellations in the particular patient's brain and simulate every possible impact of removing the selected node 410A-N or edge 412A-N on those determined parcellations. The global efficiency metrics 414 can be updated in real-time to reflect global efficiency data about a particular node 410A-N or edge 412A-N that is selected (or hovered over) by the medical professional. In some implementations, the global efficiency metrics 414 can be presented in a separate interface, in a pop out window, and/or in another panel on the GUI 400. Sometimes, global efficiency metrics 414, such as average global efficiency, can be determined using known techniques then presented in the GUI 400. The simulated impacts can be presented in the global efficiency metrics 414. The simulated impacts can also be presented in a variety of other ways to the medical professional, such as in a pop out window, another panel in the GUI 400, and/or another interface/GUI. In the global efficiency metrics 414 on the GUI 400, the simulated impacts can be represented in a bar graph. One or more other graphical and/or numeric depictions can be outputted to depict the simulated impacts. The medical professional can then use this information (e.g., the global efficiency metrics 414, the simulated impacts) to determine alternative ways and/or steps that can be taken during a medical procedure to avoid any of the negative consequences that may result for the particular patient.

The GUI 400 can also output an object creation panel 416 and/or a patient information panel 418. The object creation panel 416 can present the medical professional with one or more export controls that allow the medical professional to determine what information or views of the particular patient's brain to create. For example, the medical professional can choose to create an object that shows centrality amongst hubs in the patient's brain. The medical professional can also choose to create an object that shows unexpected centrality amongst hubs in the patient's brain. One or more other object creation options can be presented to the medical professional.

Creating the object can include overlaying particular nodes on the glass brain 408 and exporting this as an object to be stored (e.g., in the data store 108) and accessed for future analysis. For example, when the medical professional selects the option to show centrality amongst the hubs, then selects the "create object" button, the computer system can load the glass brain 408 with overlaid nodes of the hubs in the GUI 400. The medical professional can then review the loaded glass brain 408 and further adjust the view of the glass brain 408, such as by selecting one or more nodes and/or edges to remove from the glass brain 408. When satisfied, the medical professional can save the view of the glass brain 408 (e.g., export to object), which can be accessed and used in the future by the medical professional and/or by other users.

When the medical professional selects the option to show unexpected centrality and then selects the "create object" button, the computer system can load the glass brain 408 with nodes and edges that correspond to only unexpected centrality. As mentioned above, the medical professional can further adjust the view of the glass brain 408 and, once satisfied, export the view of the glass brain 408 so that it can be used in future analysis.

In some implementations, the computer system can initially load the glass brain 408 with nodes and edges that show both centrality and unexpected centrality. The computer system can calculate centrality using one or more known techniques, including but not limited to a PageRank algorithm. For example, the computer system can determine a measure of centrality for each region of the brain represented by a respective node. The system can determine the PageRank of each node. The computer system can then rank the regions of the brain according to their respective measures of centrality to generate a respective centrality rank for each region of the brain. Ranking of the nodes can also be according to one or more of: a PageRank of the node, a degree of the node (which measures a number of edges incident to the node), a strength of the node (which measures a sum of the edges incident to the node), a betweenness of the node (which measures a number of shortest paths between respective pairs of nodes in the graph that pass through the node), or a closeness of the node (which measures a reciprocal of the sum of the lengths of the shortest paths between the node and each other node in the graph). The determined centrality ranking can then be used to generate the glass brain 408 with the nodes and edges corresponding to the particular patient's brain.

One or more other default configurations can also be provided in the GUI 400 upon start of the GUI 400 and/or upon loading new patient brain data.

The patient information panel 418 can include information that is associated with the particular patient. Sometimes, image data that is used to determine nodes of the particular patient's brain can include patient identifying information. The patient identifying information can be processed out of the image data by the computer system 106 (e.g., refer to FIG. 2). Some or all of the patient identifying information can be presented in the patient information panel 418. As an example, the panel 418 can include information such as the patient's name, a patient ID, date of birth, and information about the scan or other brain image data (e.g., date of scan, ID of the scan, location where the scan was taken, etc.). Other information can also be presented in the panel 418 that may be related to the particular patient's medical visit and/or medical history/records (e.g., medications that the patient is taking, allergies of the patient, etc.). In some implementations, for example where the patient brain data is used for medical research purposes rather than diagnosis and/or treatment of the particular patient, patient information may not be presented in the GUI 400 in order to preserve patient privacy.

The GUI 400 can provide additional functionality to the medical professional. For example, the GUI 400 can provide options for the medical professional to select image data of a particular patient's brain, which can then be used to identify the patient's brain connectivity data and map the nodes and edges of the patient's brain onto the glass brain 408. This brain image data can also be used to label or otherwise identify deep and lateral structures in the particular patient's brain, which can be used by the computer system to present different views of the glass brain 408 in the GUI 400.

The GUI 400 can also present options to the medical professional to select nodes and/or edges overlaid on the glass brain 408, review their selection(s), and then export results of such selection(s). One or more other options can be provided to the medical professional with regards to selecting regions of the patient's brain, network selection, accessory language, auditory, CEN, DAN, DMN, language, limbic, limbic/paralimbic, multiple demand, salience, sensorimotor, subcortical, VAN, and visual. One or more of the abovementioned options can also be locked (e.g., represented by a lock icon), which means that the medical professional may not configure such options. One or more of the abovementioned options can also be expandable (e.g., represented by a plus icon), which means that the medical professional may configure additional related options. For example, the plus icon can provide the medical professional with functionality to expand a selected network into subnetworks. As a result, the medical professional can perform more granular subsetting and select features for even greater specificity. One or more other user-selectable options can be provided in the GUI 400 to improve or otherwise expand user functionality.

FIG. 4B depicts an updated GUI 400 based on received user input. In this example, the medical professional provided input that includes selecting one of the options 406A-N to view the right side of the particular patient's brain. The GUI 400 is automatically updated by the computer system 106 to depict the right side of the patient's brain 408A in full brightness and opacity (e.g., a brightness setting that is greater than a predetermined threshold brightness level, such as 50%, and an opacity setting that is greater than a predetermined threshold opacity level, such as 50%). The left side of the patient's brain 408B is depicted in lower brightness settings and lower opacity (e.g., a brightness setting that is less than a predetermined threshold brightness level, such as less than 50% brightness, and an opacity setting that is less than a predetermined threshold opacity level, such as less than 50% opacity). In some implementations, the left side of the patient's brain 408B can be depicted at a brightness setting and/or opacity level that is 50% less than the brightness setting and/or opacity level of the right side of the patient's brain 408A. In the example of FIG. 4B, the left side of the brain 408B is depicted as almost transparent with nodes and edges, such as node 410A and edge 412A, shaded darker, albeit still visible. As a result, the medical professional can still view nodes, edges, and structures of the left side of the brain 408B relative to the nodes, edges, and structures of the right side of the brain 408A. However, the medical professional can focus on nodes, edges, and structures of the right side of the brain 408A since they are more visible than the left side of the brain 408B. This view is advantageous because the medical professional can view the right side of the brain 408A in context with the left side of the brain 408B. The medical professional can view and analyze how one or more nodes and/or edges of the right side of the brain 408A may interact with nodes and/or edges of the left side of the brain 408B to make more informed decisions about the FIG. 4C depicts an updated GUI 400 based on received user input.

Here, the user has selected the option 406N to view deep structures in the particular patient's brain. As described above, when user input is received, the computer system can automatically update the GUI 400 to provide a seamless transition of information that is presented and outputted at the user device (e.g., the user device 104 in FIGS. 1-2). Seamless and automatic updates to the glass brain 408 in the GUI 400 can be beneficial to make the GUI 400 more intuitive and user-friendly.

Since the medical professional has selected option 406N to view deep structures in the particular patient's brain, the glass brain 408 has been updated to depict deep structures in a first indicia and non-deep structures (e.g., lateral structures) in a second indicia. The first indicia can be highest brightness settings and/or opacity level, such as 100% brightness and/or opacity level. The second indicia can be a lower brightness setting and/or opacity level, such as 50% brightness and/or opacity level. One or more other brightness and/or opacity levels can be utilized. Brightness can be a measure of intensity of features that are depicted. Therefore, a highest brightness can be a greatest intensity that the deep structures are displayed on the glass brain 408 (e.g., 100% brightness). The greatest intensity display can depict the deep structures clearly, with highest lighting, highest opacity levels, and/or highest (or normal) contrast. A lowest brightness can be a lowest intensity that the non-deep structures are displayed on the glass brain 408 (e.g., 50% brightness and/or another brightness level that is less than 100% brightness). The lowest intensity display can depict the non-deep structures in darker lighting, with lower opacity levels, and/or with less contrast. The brightness settings can be adjusted on a sliding scale between the highest setting and the lowest setting.

As shown in FIG. 4C, the patient's insula 414 is a deep structure that is depicted in the first indicia. All other structures, including nodes and edges, in the patient's brain are depicted in the second indicia. Any deep structures in the patient's brain can be labeled as such. As a result, the computer system can identify which structures have been labeled as deep structures and then present those labeled structures in the first indicia.

The insula 414 and other deep structures can be automatically labeled by the computer system before the patient's brain data is mapped onto the glass brain 408. Sometimes, ground truth source data that is used to visualize the patient's brain data on the glass brain 408 can already include labeled and annotated deep structures. Sometimes, a user, such as a medical professional, can manually label deep structures before the patient's brain data is mapped onto the glass brain 408.

As shown in FIG. 4C, the insula 414 is depicted in the first indicia, which can be highest brightness settings and/or highest opacity (e.g., 100% brightness and/or opacity). Non-deep structures are depicted in the second indicia, which can be lower brightness settings and/or lower opacity than the first indicia (e.g., 50% brightness and/or opacity). The node 410N and edge 412N are not part of the insula 414. Since they are not part of the insula 414 (a deep structure), the node 410N and edge 412N are shaded darker and more transparent than nodes and edges that are part of the deep structure. The medical professional can still view the node 410N and edge 412N to analyze connectivity amongst different nodes and edges in the patient's brain. Therefore, the medical professional can more accurately visualize associations between nodes and edges of deep and lateral structures and make more informed decisions about the particular patient's diagnosis, treatment, and/or medical procedure(s).

Still referring to FIG. 4C, the insula 414 includes multiple nodes, such as the node 410A, and multiple edges, such as the edge 412A. Although only the nodes and edges in the insular 414 are depicted in the first indicia, the medical professional can still view connectivity data between those nodes and edges and nodes and edges in non-deep structures. The medical professional can have a more wholesome understanding of how connectivity data associated with the insula 414 is related to other structures of the brain, instead of having just an isolated view and understanding of the insula 414.

Although deep structures, lateral structures, nodes, and edges are depicted in FIGS. 4A-C in one or more indicia (e.g., brighter settings and opacity for selected portions of the brain, lower brightness and opacity for unselected portions of the brain, a first color for nodes, a second color for edges, etc.), other indicia can also be used to represent these features on the glass brain 408. As an illustrative example, deep nodes can be represented in a first color, lateral nodes can be represented in a second color, edges connecting deep nodes can be represented in a third color, edges connecting lateral nodes can be represented in a fourth color, and edges connecting lateral and deep nodes can be represented in a fifth color. Other indicia are also possible.

Figure 5A:
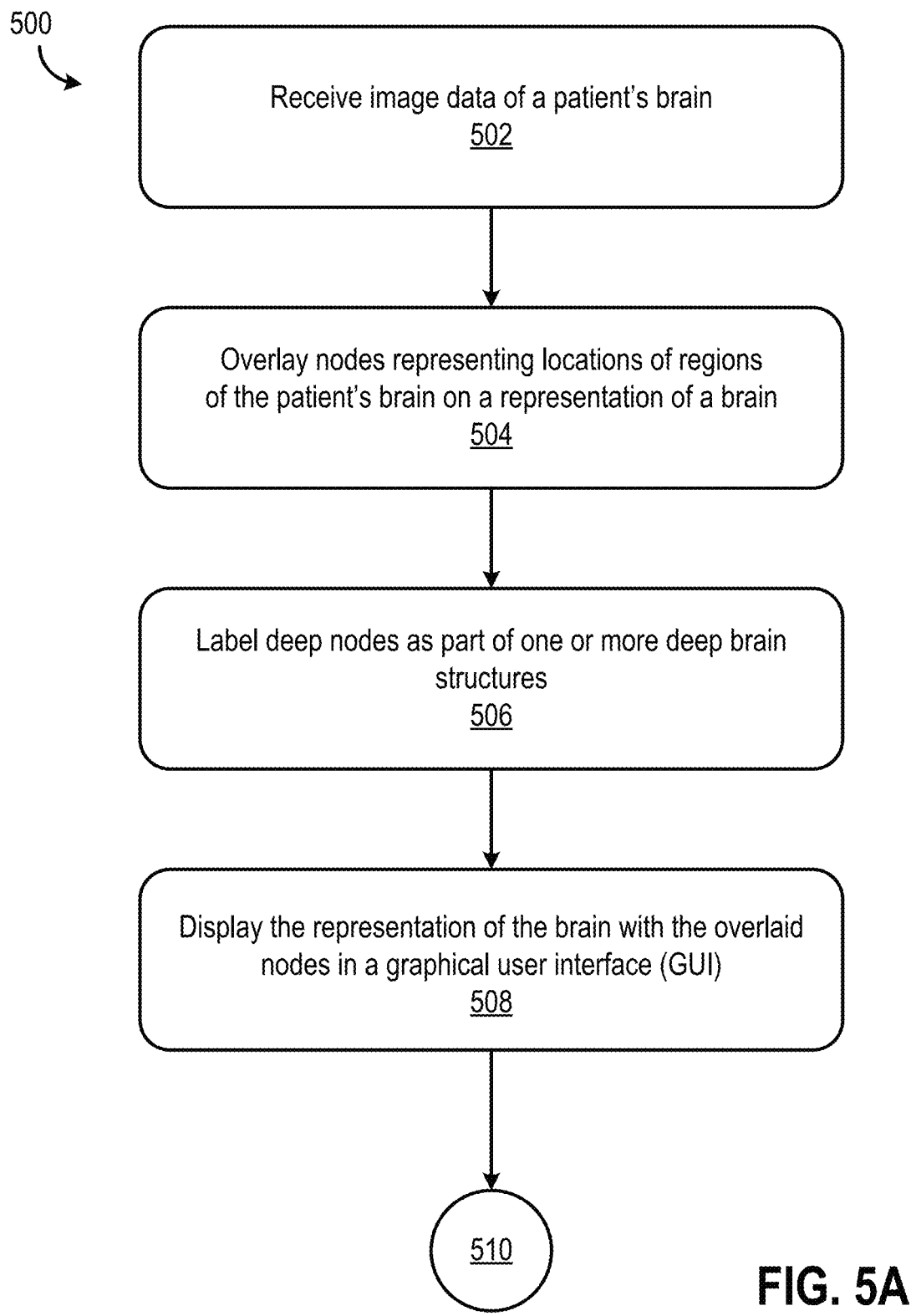
FIGS. 5A-B is a flowchart of a process for generating GUI displays of the particular brain having deep structures therein.
Figure 5B:
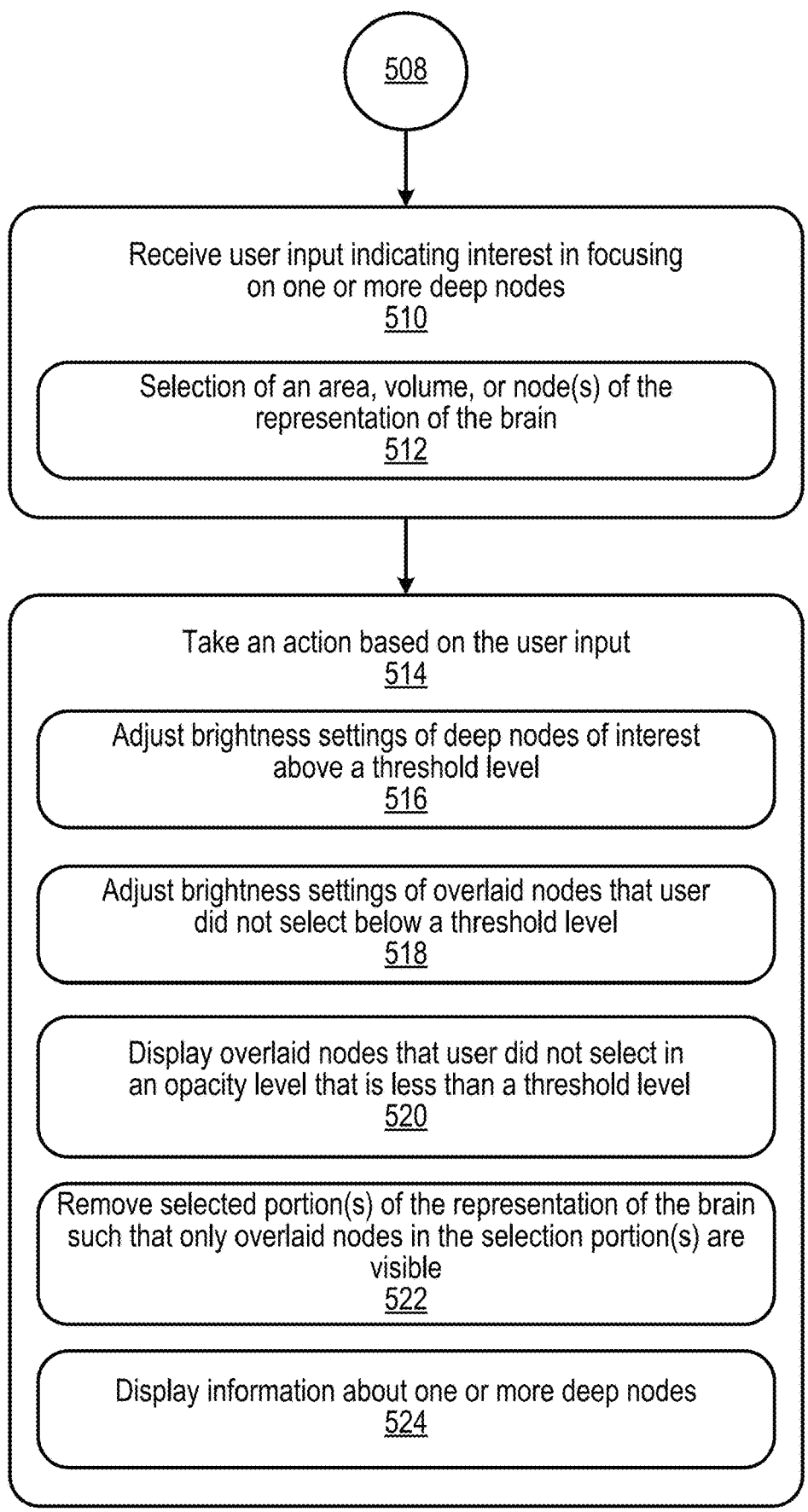

FIGS. 5A-B is a flowchart of a process 500 for generating GUI displays of the particular brain having deep structures therein. The process 500 can be performed by the computer system 106 (e.g., refer to FIGS. 1-2). Sometimes, the process 500 can be performed by the user device 104. In yet some implementations, the process 500 can be performed by another computer system, computer, device, server, network of devices, network of computers, or combination thereof. For illustrative purposes, the process 500 is described from a perspective of a computer system.

Referring to the process 500 in both FIGS. 5A-B, the computer system can receive image data of a patient's brain in 502. The image data can be received from a medical imaging device (e.g., the medical imaging device 110 in FIGS. 1-2). The image data can also be received from a user device (e.g., the user device 104 in FIGS. 1-2). Sometimes, the computer system can retrieve, from a data store (e.g., the data store 108 in FIGS. 1-2), image data of the patient's brain. The image data can include structures (deep and lateral), parcellations, hubs, etc. of the patient's brain that have been annotated and labeled. These features of the brain can be manually annotated and labeled by a medical professional (e.g., clinician) or other user. The features of the brain can also be automatically annotated and labeled by a computer system (e.g., the computer system 106) using one or more machine learning trained models, algorithms, techniques, and/or processes. The features of the brain can be automatically annotated and labeled based on identifying proximity of nodes to a cortical surface of the brain. A node can be annotated and labeled as a lateral node (e.g., shallow) based on having greater proximity (e.g., a distance within a predetermined threshold range) to the cortical surface of the brain. A node can be annotated and labeled as a deep node based on having less proximity (e.g., the distance exceeds the predetermined threshold range) to the cortical surface of the brain. The image data can include other/additional information about the patient, such as their name, a patient ID, a date of birth, a date that the image data was captured/recorded, and/or other relevant medical information (e.g., refer to FIGS. 3-4). As described herein, the other information can be presented in a GUI at the user device in a panel, pop out window, or other portion of the GUI so as to not interfere or overlap with a representation of the patient's brain.

In 504, the computer system can overlay nodes representing locations of regions of the patient's brain on a representation of a brain. The regions can include hubs, parcellations, or other structures in the patient's brain. The image data can include connectivity data that is used to overlay the nodes on the representation of the brain. Overlaying the nodes on the representation of the brain can be performed as described throughout this disclosure. Overlaying the nodes can include connecting both deep and lateral nodes by edges. The edges represent fibers in the patient's brain. The representation of the brain can be a glass brain (e.g., refer to FIGS. 3-4). The same glass brain can be used for all patient brains. One or more other types of representations of the brain can be used to visually depict the various regions in the particular patient's brain and the connectivity data associated with such regions.

Next, the computer system can label deep nodes as part of one or more deep brain structures (506). The deep brain structures can include at least one of a group of insula, lobes, and subcortical structures. As mentioned above, in some implementations, the deep nodes and/or deep structures can already be annotated and labeled in brain image data that is used to overlay the nodes on the representation of the brain. In some implementations, the deep nodes and/or structures can be labeled by the computer system using one or more machine learning models, techniques, and/or algorithms to identify deep structures and label them as such. Sometimes, the deep nodes and/or structures may already be labeled in the brain image data (e.g., automatically by the computer system 106 or some other computer or device, manually by a user, etc.). Thus, the computer system can skip block 506 and proceed to block 508 in the process 500. Furthermore, as described herein, labeling is advantageous so that the computer system can accurately identify which structures should be displayed on the glass brain in one or more different indicia (e.g., structures that are labeled as deep structures can be depicted at full brightness and opacity while structures that are not labeled as deep structures can be depicted at lower brightness and more transparency).

In 508, the computer system can display the representation of the brain with the overlaid nodes in a GUI (508). Sometimes, the computer system can display a graph with edges of correlation. Refer to FIGS. 4A-C for further discussion about the GUI. As described above, the nodes can be displayed in one or more different indicia to assist the medical professional in visualizing different structures of the particular patient's brain. Moreover, a default view can include all nodes overlaid on a glass brain, which can inherently prioritize and display lateral nodes over deep nodes.

The computer system can receive user input indicating an interest in focusing on one or more deep nodes (510). In other words, the medical professional can provide input to the user device that includes selection of a region of interest on the glass brain. The region of interest can be one or more deep nodes, one or more lateral nodes, edges, one or more sides of the brain, one or more lateral structures and/or one or more deep structures. The region of interest can be any structure or portion of the brain that can be challenging to visualize due to an abundance of overlaid nodes, edges, and structures (such as midline nodes and carious other lobes or structures in the brain). The user input can include selection of an area, volume, or node(s) of the representation of the brain (512). Sometimes, the user input can include hovering over one or more of the overlaid nodes of interest or structures in the brain. The user input can be made by the medical professional or other user at the user device (e.g., the user device 104 in FIGS. 1-2).

As an example, the medical professional can select an option to view deep nodes of the particular patient's brain. As a result, the computer system can display only the deep structures of the patient's brain in a bright setting or other visual setting that highlights or emphasizes the deep structures over the non-deep structures (e.g., lateral structures). Thus, selection of the deep structures can cause the computer system to adjust visual settings of the non-deep structures. If the deep structures are already visually depicted in brightest settings and/or opacity, the computer system can respond to the user input by reducing brightness settings and/or opacity of the non-selected structures (e.g., lateral or non-deep structures). Accordingly, non-deep structures can be darkened (e.g., lower brightness setting) and/or displayed in a lower opacity such that they are not as visible as the deep structures. This allows for all of the brain data of the particular patient to be analyzed with the non-deep structures reduced in visibility such that the medical professional can focus on the deeper structures. This view can be especially beneficial when lateral nodes, edges, and structures may otherwise obstruct views of the deeper nodes, edges, and structures.

As an illustrative example, the medical professional can click on one or more nodes that the medical professional would consider removing during an actual surgical procedure for that patient. The selected nodes can then be displayed in another GUI to provide the medical professional with a more detailed view of such nodes and/or effects of removing such nodes on other regions or structures of the brain. The selected nodes can also be displayed in a different indicia than unselected portions of the patient's brain in order to depict associations between the selected nodes and unselected portions or regions of the patient's brain. Depicting these associations can be beneficial to assist the medical professional in more accurately analyzing the particular patient's brain and making decisions about the patient's diagnosis, treatment, condition, therapy, and/or medical procedure.

Based on the user input, the computer system can take some action on the representation of the brain in 514. For example, the computer system can adjust brightness settings of deep nodes of interest above a threshold level in 516. If the deep nodes are already depicted in a highest brightness setting or the deep nodes are already depicted in a brightness that exceeds the threshold level (e.g., 50% threshold level), then the computer system may not have to take an action such as that in block 516.

The computer system can adjust brightness settings of overlaid nodes that the user did not select below a threshold level (518). For example, when the user selects an option to view deep structures, any lateral structures in the particular patient's brain can be depicted in a lowest brightness setting or a brightness setting that is lower than the brightness settings of deep structures (e.g., a brightness setting that is less than the predetermined threshold level, such as less than 50% brightness). For example, as depicted in FIGS. 4B-C, lateral structures, including lateral nodes and edges, can be depicted in a darker shade (e.g., lower brightness setting) than deep structures, such as the patient's insula. As a result, the medical professional can view interaction and connectivity between both deep and lateral structures in the patient's brain with more emphasis and focus on the deep structures in the patient's brain. This view can be beneficial to assist the medical professional in more accurately analyzing and understanding deep and lateral structures in the patient's brain and relationships amongst such structures (e.g., connectivity).

The computer system can display overlaid nodes that the user did not select in an opacity level that is less than a threshold level in 520. For example, when the user selects an option to view deep structures, the representation of the brain can be automatically updated to depict nodes and edges of the lateral structures in a lower opacity level than nodes and edges of the deep structures. The nodes and edges of the lateral structures can, for example, be depicted as less than 50% opacity. Such nodes and edges can be more transparent so that they are still visible but not a primary visual focus. The medical professional can therefore focus on the nodes and edges of the deep structures while still being able to visualize connectivity data and other relationships with the nodes and edges of lateral structures.

The computer system can also remove selected portions of the representation of the brain such that only overlaid nodes in the selected portion are visible in 522. The representation of the brain can be updated to show only connectivity amongst nodes without the glass brain. In other words, and as an illustrative example, by selecting the right side of the brain, the glass brain can be updated to depict only the nodes connected by edges in the right side of the brain. The glass brain depiction may be removed from the display and/or can be depicted in a lower brightness setting and/or opacity level. Therefore, the medical professional can visually focus on connections between nodes in the right side of the brain and may not be overwhelmed by other structures appearing in the right side of the brain.

Sometimes, the computer system can display information about one or more deep nodes in 524. For example, the computer system can calculate and display an impact of excising a selected portion, area, or volume from the representation of the brain. Sometimes, the impact of excising the selected portion of the brain can include interference(s) on cognitive functionality of the patient's brain. Thus, excising the selected portion of the brain can have detrimental effects on lateral and/or deep structures of the particular patient's brain. The computer system can generate output indicating whether the particular patient would be impaired by removal of the user-selected portion of the brain.

The output can be presented to the medical professional as text. The text can indicate what type of cognitive impairment is likely for the particular patient. The text can overlay a portion of the GUI and/or the representation of the brain. The text can also be presented in a separate interface, window, or pop out window. Sometimes, the output can be presented to the medical professional as a visual modification of the representation of the brain. In other words, if the user-selected portion of the brain is removed but nodes in that portion of the brain connect to nodes in other portions of the brain, then the computer system can update the representation of the brain to show connected edges, nodes, hubs, and/or parcellations of the brain also being cut or otherwise affected. The output can also be presented as global efficiency metrics, as described in reference to FIGS. 4A-C.

Sometimes, displaying information about the one or more nodes can include outputting additional information about the particular node(s) in the GUI. For example, when the medical professional hovers over the node(s), the computer system can present information about the node(s) over a portion of the GUI. Sometimes, this information can be displayed in a separate window, a pop-out panel, or another GUI. The information can indicate connectivity data, centrality data, name of the node, weight of the node, and other information about the node, structure, parcellation, hub, and/or edges that can be used by the medical professional to make informed decisions for diagnosis, treatment, procedures, and other medical research or analysis.

As yet another example, the computer system can load, in a brain atlas form, one or more structures, nodes, or edges that are selected or clicked on by the medical professional. The medical professional can, for example, select one or more deep nodes that the medical professional would like to view in isolation. As a result, the medical professional can focus more on the particular deep node of interest. The selected node can be loaded in another window or GUI with the corresponding parcellation or parcellation/track combination.

As another example, the computer system can display first and second portions of the representation of the brain with the overlaid nodes. The first portion can be a right side of the patient's brain and the second portion can be a left side of the patient's brain. The computer system can receive user input indicating selection of one of the first and second portions of the representation of the brain. For example, the user can select an option to view only one side of the patient's brain, such as the right side of the brain. In response to receiving the user input, the computer system can remove the selected one of the first and second portions of the brain such that only the overlaid nodes in the selected one of the first and second portions of the representation of the brain are visible. In other words, the computer system can display just the nodes and edges in the particular selected portion of the brain. As another example, the computer system can display just the selected portion of the brain with the nodes and edges of that portion. As yet another example, the computer system can display the selected portion of the brain in a first indicia and the unselected portion of the brain in a second indicia. In other words, the unselected portion of the brain can be shaded (e.g., lower brightness setting, lower opacity) but still visible so that the medical professional can view connectivity between structures, nodes, and edges of the selected portion of the brain with structures, nodes, and edges of the unselected portion of the brain.

For example, if the medical professional selected the right side of the patient's brain, then the computer system can update the representation of the brain to include only nodes and edges that are part of the right side of the brain. The left side of the brain can still be displayed on the glass representation of the brain with all nodes and edges therein. By viewing just the nodes and edges in the selected portion of the brain, the medical professional can more easily view connectivity data and other information associated with edges and nodes in the selected portion of the brain. Although the medical professional may focus on the selected portion of the brain, the medical professional can also more easily visualize relationships between structures, edges, and nodes of the selected portion of the brain with structures, edges, and nodes of the unselected portion(s) of the brain.

Figure 6:
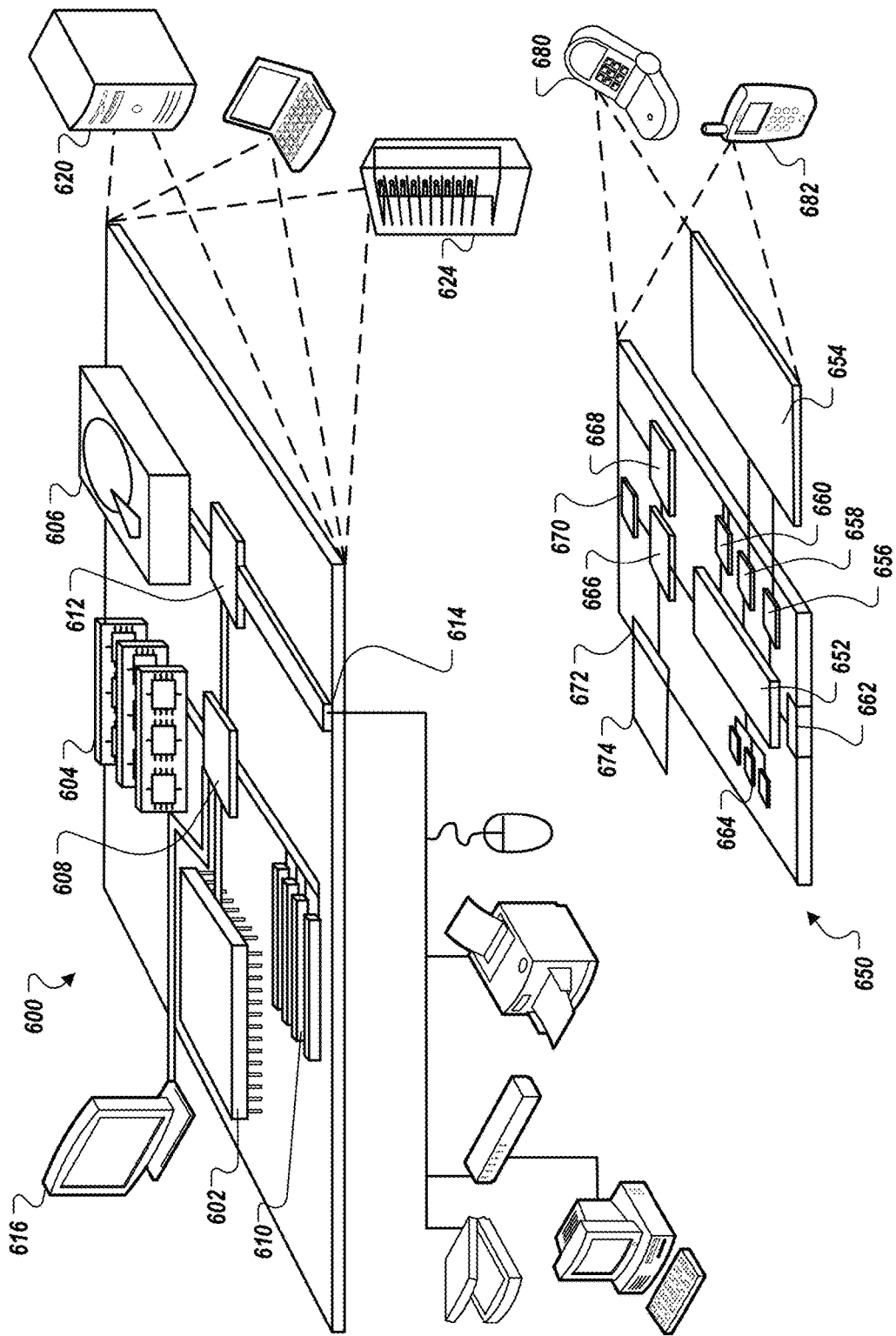
FIG. 6 is a schematic diagram that shows an example of a computing device and a mobile computing device.

FIG. 6 shows an example of a computing device 600 and an example of a mobile computing device that can be used to implement the techniques described here. The computing device 600 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 600 includes a processor 602, a memory 604, a storage device 606, a high-speed interface 608 connecting to the memory 604 and multiple high-speed expansion ports 610, and a low-speed interface 612 connecting to a low-speed expansion port 614 and the storage device 606. Each of the processor 602, the memory 604, the storage device 606, the high-speed interface 608, the high-speed expansion ports 610, and the low-speed interface 612, are interconnected using various busses, and can be mounted on a common motherboard or in other manners as appropriate. The processor 602 can process instructions for execution within the computing device 600, including instructions stored in the memory 604 or on the storage device 606 to display graphical information for a GUI on an external input/output device, such as a display 616 coupled to the high-speed interface 608. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 604 stores information within the computing device 600. In some implementations, the memory 604 is a volatile memory unit or units. In some implementations, the memory 604 is a non-volatile memory unit or units. The memory 604 can also be another form of computer-readable medium, such as a magnetic or optical disk.

The storage device 606 is capable of providing mass storage for the computing device 600. In some implementations, the storage device 606 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 604, the storage device 606, or memory on the processor 602.

The high-speed interface 608 manages bandwidth-intensive operations for the computing device 600, while the low-speed interface 612 manages lower bandwidth-intensive operations. Such allocation of functions is exemplary only. In some implementations, the high-speed interface 608 is coupled to the memory 604, the display 616 (e.g., through a graphics processor or accelerator), and to the high-speed expansion ports 610, which can accept various expansion cards (not shown). In the implementation, the low-speed interface 612 is coupled to the storage device 606 and the low-speed expansion port 614. The low-speed expansion port 614, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 600 can be implemented in a number of different forms, as shown in the figure. For example, it can be implemented as a standard server 620, or multiple times in a group of such servers. In addition, it can be implemented in a personal computer such as a laptop computer 622. It can also be implemented as part of a rack server system 624. Alternatively, components from the computing device 600 can be combined with other components in a mobile device (not shown), such as a mobile computing device 650. Each of such devices can contain one or more of the computing device 600 and the mobile computing device 650, and an entire system can be made up of multiple computing devices communicating with each other.

The mobile computing device 650 includes a processor 652, a memory 664, an input/output device such as a display 654, a communication interface 666, and a transceiver 668, among other components. The mobile computing device 650 can also be provided with a storage device, such as a micro-drive or other device, to provide additional storage. Each of the processor 652, the memory 664, the display 654, the communication interface 666, and the transceiver 668, are interconnected using various buses, and several of the components can be mounted on a common motherboard or in other manners as appropriate.

The processor 652 can execute instructions within the mobile computing device 650, including instructions stored in the memory 664. The processor 652 can be implemented as a chipset of chips that include separate and multiple analog and digital processors. The processor 652 can provide, for example, for coordination of the other components of the mobile computing device 650, such as control of user interfaces, applications run by the mobile computing device 650, and wireless communication by the mobile computing device 650.

The processor 652 can communicate with a user through a control interface 658 and a display interface 656 coupled to the display 654. The display 654 can be, for example, a TFT (Thin-Film-Transistor Liquid Crystal Display) display or an OLED (Organic Light Emitting Diode) display, or other appropriate display technology. The display interface 656 can comprise appropriate circuitry for driving the display 654 to present graphical and other information to a user. The control interface 658 can receive commands from a user and convert them for submission to the processor 652. In addition, an external interface 662 can provide communication with the processor 652, so as to enable near area communication of the mobile computing device 650 with other devices. The external interface 662 can provide, for example, for wired communication in some implementations, or for wireless communication in other implementations, and multiple interfaces can also be used.

The memory 664 stores information within the mobile computing device 650. The memory 664 can be implemented as one or more of a computer-readable medium or media, a volatile memory unit or units, or a non-volatile memory unit or units. An expansion memory 674 can also be provided and connected to the mobile computing device 650 through an expansion interface 672, which can include, for example, a SIMM (Single In Line Memory Module) card interface. The expansion memory 674 can provide extra storage space for the mobile computing device 650, or can also store applications or other information for the mobile computing device 650. Specifically, the expansion memory 674 can include instructions to carry out or supplement the processes described above, and can include secure information also. Thus, for example, the expansion memory 674 can be provide as a security module for the mobile computing device 650, and can be programmed with instructions that permit secure use of the mobile computing device 650. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 664, the expansion memory 674, or memory on the processor 652. In some implementations, the computer program product can be received in a propagated signal, for example, over the transceiver 668 or the external interface 662.

The mobile computing device 650 can communicate wirelessly through the communication interface 666, which can include digital signal processing circuitry where necessary. The communication interface 666 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 668 using a radio-frequency. In addition, short-range communication can occur, such as using a Bluetooth, WiFi, or other such transceiver (not shown). In addition, a GPS (Global Positioning System) receiver module 670 can provide additional navigation- and location-related wireless data to the mobile computing device 650, which can be used as appropriate by applications running on the mobile computing device 650.

The mobile computing device 650 can also communicate audibly using an audio codec 660, which can receive spoken information from a user and convert it to usable digital information. The audio codec 660 can likewise generate audible sound for a user, such as through a speaker, e.g., in a handset of the mobile computing device 650. Such sound can include sound from voice telephone calls, can include recorded sound (e.g., voice messages, music files, etc.) and can also include sound generated by applications operating on the mobile computing device 650.

The mobile computing device 650 can be implemented in a number of different forms, as shown in the figure. For example, it can be implemented as a cellular telephone 680. It can also be implemented as part of a smart-phone 682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other. In some implementations, the computing system can be cloud based and/or centrally processing data. In such case anonymous input and output data can be stored for further analysis. In a cloud based and/or processing center set-up, compared to distributed processing, it can be easier to ensure data quality, and accomplish maintenance and updates to the calculation engine, compliance to data privacy regulations and/or troubleshooting.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A method comprising:
    receiving brain data for a patient, the brain data including a plurality of nodes in the patient's brain and connectivity data amongst the plurality of nodes, wherein the plurality of nodes represent a plurality of brain structures;
    labeling first nodes in the plurality of nodes as deep nodes based on the first nodes having a distance to a cortical surface of the patient's brain that exceeds a threshold distance range;
    labeling second nodes in the plurality of nodes as lateral nodes based on the second nodes having a distance to the cortical surface of the patient's brain that is within the threshold distance range;
    overlaying the deep nodes, the lateral nodes, and the connectivity data between the deep nodes and the lateral nodes on a three-dimensional (3D) representation of a brain;
    displaying the 3D representation of the brain with the overlaid deep nodes, the overlaid lateral nodes, and the connectivity data in a graphical user interface (GUI);
    receiving user input indicating selection of at least one of the overlaid deep nodes; and
    based on the user input, adjusting at least one of brightness and opacity of the selected at least one overlaid deep node to cause the selected at least one overlaid deep node to be more visually apparent than non-selected overlaid deep nodes and the overlaid lateral nodes on the 3D representation of the brain,
    wherein the adjusted at least one overlaid deep node is displayed, on the 3D representation of the brain, concurrently with (i) the non-selected overlaid deep nodes, (ii) the overlaid lateral nodes, and (iii) the connectivity data between the adjusted at least one overlaid deep node and (i)-(ii).

2. The method of claim 1, further comprising labeling the deep nodes as part of one or more deep brain structures.

3. The method of claim 2, wherein the deep brain structures include at least one of a group of insula, lobes, and subcortical structures.

4. The method of claim 1, wherein the plurality of nodes further represent locations of regions of the patient's brain, wherein the regions include parcellations of the patient's brain.

5. The method of claim 1, wherein, based on the user input, adjusting at least one of brightness and opacity of the selected at least one overlaid deep node further comprises displaying the non-selected overlaid nodes at an opacity level that is less than a predetermined threshold.

6. The method of claim 1, wherein, based on the user input, adjusting at least one of brightness and opacity of the selected at least one overlaid deep node further comprises adjusting brightness of the non-selected overlaid nodes such that the brightness of the non-selected overlaid nodes is less than the brightness of the selected at least one overlaid deep node by a predetermined threshold.

7. The method of claim 1, further comprising:
displaying first and second portions of the 3D representation of the brain with the overlaid deep nodes and the overlaid lateral nodes;
receiving user input indicating selection of one of the first and second portions of the 3D representation of the brain; and
in response to receiving the user input, removing the selected one of the first and second portions of the 3D representation of the brain such that only the overlaid deep nodes and the overlaid lateral nodes in the selected one of the first and second portions of the 3D representation of the brain are visible.

8. The method of claim 7, wherein the first portion of the 3D representation of the brain represents a right side of the patient's brain and the second portion of the 3D representation of the brain represents a left side of the patient's brain.

9. The method of claim 1, further comprising, based on the user input, displaying information about the at least one overlaid node over a portion of the GUI.

10. The method of claim 1, further comprising, based on the user input, displaying information about the at least one overlaid deep node in a second GUI.

11. A method comprising:
receiving brain data for a patient, the brain data including a plurality of nodes in the patient's brain and connectivity data amongst the plurality of nodes, wherein the plurality of nodes represent a plurality of brain structures;
labeling first nodes in the plurality of nodes as deep nodes based on the first nodes having a distance to a cortical surface of the patient's brain that exceeds a threshold distance range;
labeling second nodes in the plurality of nodes as lateral nodes based on the second nodes having a distance to the cortical surface of the patient's brain that is within the threshold distance range;
overlaying the deep nodes, the lateral nodes, and the connectivity data between the deep nodes and the lateral nodes on a three-dimensional (3D) representation of a brain;
displaying the 3D representation of the brain with the overlaid deep nodes, the overlaid lateral nodes, and the connectivity data in a graphical user interface (GUI);
receiving user input indicating selection of at least one of the overlaid deep nodes; and
based on the user input, adjusting at least one of brightness and opacity of the selected at least one overlaid deep node to cause the selected at least one overlaid deep node to be more visually apparent than non-selected overlaid deep nodes and the overlaid lateral nodes on the 3D representation of the brain,
wherein the adjusted at least one overlaid deep node is displayed, on the 3D representation of the brain, concurrently with (i) the non-selected overlaid deep nodes, (ii) the overlaid lateral nodes, (iii) the connectivity data between the adjusted at least one overlaid deep node and the non-selected overlaid deep nodes, and (iv) the connectivity data between the adjusted at least one overlaid node and the overlaid lateral nodes.

12. The method of claim 11, further comprising labeling the deep nodes as part of one or more deep brain structures.

13. The method of claim 12, wherein the deep brain structures include at least one of a group of insula, lobes, and subcortical structures.

14. The method of claim 11, wherein, based on the user input, adjusting at least one of brightness and opacity of the selected at least one overlaid deep node further comprises displaying the non-selected overlaid nodes at an opacity level that is less than a predetermined threshold.

15. The method of claim 11, wherein, based on the user input, adjusting at least one of brightness and opacity of the selected at least one overlaid deep node further comprises adjusting brightness of the non-selected overlaid nodes such that the brightness of the non-selected overlaid nodes is less than the brightness of the selected at least one overlaid deep node by a predetermined threshold.

16. The method of claim 11, further comprising:
displaying first and second portions of the 3D representation of the brain with the overlaid deep nodes and the overlaid lateral nodes;
receiving user input indicating selection of one of the first and second portions of the 3D representation of the brain; and
in response to receiving the user input, removing the selected one of the first and second portions of the 3D representation of the brain such that only the overlaid deep nodes and the overlaid lateral nodes in the selected one of the first and second portions of the 3D representation of the brain are visible.

17. The method of claim 16, wherein the first portion of the 3D representation of the brain represents a right side of the patient's brain and the second portion of the 3D representation of the brain represents a left side of the patient's brain.

18. The method of claim 11, further comprising, based on the user input, displaying information about the at least one overlaid node over a portion of the GUI.

19. The method of claim 11, further comprising, based on the user input, displaying information about the at least one overlaid deep node in a second GUI.

20. A system comprising:
at least one programmable processor; and
a machine-readable medium storing instructions that, when executed by the at least one programmable processor, cause the at least one programmable processor to perform operations comprising:
receiving brain data for a patient, the brain data including a plurality of nodes in the patient's brain and connectivity data amongst the plurality of nodes, wherein the plurality of nodes represent a plurality of brain structures;
labeling first nodes in the plurality of nodes as deep nodes based on the first nodes having a distance to a cortical surface of the patient's brain that exceeds a threshold distance range;
labeling second nodes in the plurality of nodes as lateral nodes based on the second nodes having a distance to the cortical surface of the patient's brain that is within the threshold distance range;
overlaying the deep nodes, the lateral nodes, and the connectivity data between the deep nodes and the lateral nodes on a three-dimensional (3D) representation of a brain;
displaying the 3D representation of the brain with the overlaid deep nodes, the overlaid lateral nodes, and the connectivity data in a graphical user interface (GUI);
receiving user input indicating selection of at least one of the overlaid deep nodes; and based on the user input, adjusting at least one of brightness and opacity of the selected at least one overlaid deep node to cause the selected at least one overlaid deep node to be more visually apparent than non-selected overlaid deep nodes and the overlaid lateral nodes on the 3D representation of the brain, wherein the adjusted at least one overlaid deep node is displayed, on the 3D representation of the brain, concurrently with (i) the non-selected overlaid deep nodes, (ii) the overlaid lateral nodes, (iii) the connectivity data between the adjusted at least one overlaid deep node and the non-selected overlaid deep nodes, and (iv) the connectivity data between the adjusted at least one overlaid node and the overlaid lateral nodes.

\* \* \* \* \*